US007223236B2

(12) United States Patent
Brown

(10) Patent No.: US 7,223,236 B2
(45) **Date of Patent: *May 29, 2007**

(54) SYSTEM AND METHOD FOR MONITORING USER-RELATED DATA FROM A PERSON

(75) Inventor: Stephen James Brown, Mountain View, CA (US)

(73) Assignee: Health Hero Network, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/221,873

(22) Filed: Sep. 9, 2005

(65) Prior Publication Data

US 2006/0009706 A1 Jan. 12, 2006

Related U.S. Application Data

(60) Division of application No. 10/605,547, filed on Oct. 7, 2003, which is a continuation of application No. 09/237,194, filed on Jan. 26, 1999, which is a continuation of application No. 08/481,925, filed on Jun. 7, 1995, now Pat. No. 5,899,855, which is a continuation of application No. 08/233,397, filed on Apr. 26, 1994, now abandoned, which is a continuation-in-part of application No. 07/977,323, filed on Nov. 17, 1992, now Pat. No. 5,307,263.

(51) Int. Cl.
*A61B 5/00* (2006.01)
*G06Q 10/00* (2006.01)
*G06Q 50/00* (2006.01)

(52) U.S. Cl. ........................... 600/300; 128/903; 705/2

(58) Field of Classification Search ........ 600/300–301; 128/903–904
See application file for complete search history.

(56) References Cited

U.S. PATENT DOCUMENTS 3,426,150 A 2/1969 Tygart
3,566,365 A 2/1971 Rawson et al.
3,566,370 A 2/1971 Worthington, Jr. et al.
3,581,072 A 5/1971 Nymeyer
3,768,014 A 10/1973 Smith
3,810,102 A * 5/1974 Parks et al. .................... 705/3

(Continued)

FOREIGN PATENT DOCUMENTS

EP 0286456 10/1988

(Continued)

OTHER PUBLICATIONS

Food Chemical News, Database Management is Key to Database Quality. Jul. 22, 1996, v38 n22.

(Continued)

*Primary Examiner*—Robert L. Nasser
(74) *Attorney, Agent, or Firm*—Christopher P. Maiorana, PC

(57) ABSTRACT

Monitoring airflow from a person is accomplished by using a central server arranged to receive and communicate data together with at least one microprocessor-based subsystem. The subsystem includes a microprocessor, a display and a memory. It presents information to the person on the display and processes a digital signal representing airflow from the person. Airflow-related data is communicated to the central server and, in turn, is communicated to at least one health care professional computer. The system can be used to realize systems for self-care monitoring and control of afflictions and physical conditions, such as chronic respiratory afflictions. The system can also be used together with other monitoring devices, such as glucose, blood pressure, pulse and temperature monitors, to monitor the person's condition and to communicate related data to the central server.

26 Claims, 6 Drawing Sheets

U.S. PATENT DOCUMENTS 3,811,116 A 5/1974 Takeuchi et al.
3,883,235 A 5/1975 Lynn et al.
3,910,257 A 10/1975 Fletcher, et al.
3,920,005 A 11/1975 Gombrich et al.
3,996,928 A 12/1976 Marx
4,004,577 A 1/1977 Sarnoff
4,051,522 A 9/1977 Healy et al.
4,060,915 A 12/1977 Conway
4,130,881 A 12/1978 Haessler et al.
4,150,284 A 4/1979 Trenkler et al.
4,151,407 A 4/1979 McBride et al.
4,151,831 A 5/1979 Lester
4,173,971 A * 11/1979 Karz .......................... 600/515
4,216,462 A 8/1980 McGrath et al.
4,227,526 A 10/1980 Goss
4,253,521 A 3/1981 Savage
4,259,548 A 3/1981 Fahey et al.
4,270,547 A 6/1981 Steffen et al.
4,296,756 A * 10/1981 Dunning et al. ............ 600/529
4,347,568 A 8/1982 Giguere et al.
4,347,851 A 9/1982 Jundanian
4,360,345 A 11/1982 Hon
4,412,287 A 10/1983 Braddock, III
4,417,306 A 11/1983 Citron et al.
4,422,081 A 12/1983 Woods
4,428,733 A 1/1984 Kumar-Misir
4,449,536 A 5/1984 Weaver
4,465,077 A 8/1984 Schneider
4,473,884 A 9/1984 Behl
4,518,361 A 5/1985 Conway
4,519,398 A 5/1985 Lisiecki et al.
4,531,527 A 7/1985 Reinhold, Jr.
4,546,436 A 10/1985 Schneider et al.
4,566,461 A 1/1986 Lubell et al.
4,576,578 A 3/1986 Parker et al.
4,592,546 A 6/1986 Fascenda et al.
4,627,445 A 12/1986 Garcia
4,674,652 A 6/1987 Aten et al.
4,686,624 A 8/1987 Blum et al.
4,694,490 A 9/1987 Harvey et al.
4,695,954 A 9/1987 Rose et al.
4,712,562 A * 12/1987 Ohayon et al. ............. 600/485
4,722,349 A 2/1988 Baumberg
4,729,381 A 3/1988 Harada et al.
4,730,253 A 3/1988 Gordon
4,731,726 A 3/1988 Allen, III
4,738,451 A 4/1988 Logg
4,768,229 A 8/1988 Benjamin et al.
4,779,199 A 10/1988 Yoneda et al.
4,782,511 A 11/1988 Nemec et al.
4,789,928 A 12/1988 Fujisaki
4,796,639 A 1/1989 Snow et al.
4,799,156 A 1/1989 Shavit et al.
4,799,199 A 1/1989 Scales, III et al.
4,803,625 A 2/1989 Fu et al.
4,807,169 A 2/1989 Overbeck
4,835,372 A * 5/1989 Gombrich et al. .......... 235/375
4,838,275 A 6/1989 Lee
4,846,797 A 7/1989 Howson et al.
4,853,521 A 8/1989 Claeys et al.
4,858,354 A 8/1989 Gettler
4,858,617 A 8/1989 Sanders
4,890,621 A 1/1990 Hakky
4,894,777 A 1/1990 Negishi et al.
4,897,869 A 1/1990 Takahashi
4,899,839 A 2/1990 Dessertine et al.
4,903,201 A 2/1990 Wagner
4,907,973 A 3/1990 Hon
4,916,441 A 4/1990 Gombrich
4,931,934 A 6/1990 Snyder
4,933,873 A 6/1990 Kaufman et al.
4,933,876 A 6/1990 Markoff et al.
4,950,246 A 8/1990 Muller
4,950,264 A 8/1990 Osborn, III
4,953,552 A 9/1990 DeMarzo
4,958,632 A 9/1990 Duggan
4,958,641 A 9/1990 Digby et al.
4,960,118 A * 10/1990 Pennock ................ 128/200.24
4,967,756 A 11/1990 Hewitt
4,977,899 A 12/1990 Digby et al.
4,978,303 A 12/1990 Lampbell
4,978,335 A 12/1990 Arthur, III
4,979,509 A 12/1990 Hakky
4,996,642 A 2/1991 Hey
5,007,429 A 4/1991 Treatch et al.
5,009,645 A 4/1991 Silver et al.
5,016,172 A 5/1991 Dessertine
5,019,974 A 5/1991 Beckers
5,024,225 A 6/1991 Fang
5,025,374 A 6/1991 Roizen et al.
5,034,807 A 7/1991 Von Kohorn
5,035,625 A 7/1991 Munson et al.
5,036,462 A * 7/1991 Kaufman et al. ........... 600/300
5,049,487 A 9/1991 Phillips et al.
5,050,612 A 9/1991 Matsumura
5,056,059 A 10/1991 Tivig et al.
5,059,394 A 10/1991 Phillips et al.
5,065,315 A 11/1991 Garcia
5,068,536 A 11/1991 Rosenthal
5,074,317 A 12/1991 Bondell et al.
5,077,476 A 12/1991 Rosenthal
5,077,665 A 12/1991 Silverman et al.
5,095,798 A 3/1992 Okada et al.
5,104,380 A 4/1992 Holman et al.
5,109,414 A 4/1992 Harvey et al.
5,109,974 A 5/1992 Beer et al.
5,111,396 A 5/1992 Mills et al.
5,111,817 A 5/1992 Clark et al.
5,111,818 A 5/1992 Suzuki et al.
5,120,230 A 6/1992 Clark et al.
5,120,421 A 6/1992 Glass et al.
5,128,552 A 7/1992 Fang et al.
5,128,752 A 7/1992 Von Kohorn
5,134,391 A 7/1992 Okada
5,142,358 A 8/1992 Jason
5,142,484 A 8/1992 Kaufman et al.
5,143,378 A 9/1992 Joel
5,171,977 A 12/1992 Morrison
5,176,502 A 1/1993 Sanderson et al.
5,182,707 A 1/1993 Cooper et al.
5,204,670 A 4/1993 Stinton
5,219,322 A 6/1993 Weathers
5,222,020 A 6/1993 Takeda
5,226,895 A 7/1993 Harris
5,227,874 A 7/1993 Von Kohorn
5,228,450 A 7/1993 Sellers
5,230,629 A 7/1993 Buschke
5,231,990 A 8/1993 Gauglitz
5,233,520 A 8/1993 Kretsch et al.
5,243,515 A 9/1993 Lee
5,249,044 A 9/1993 Von Kohorn
5,251,126 A 10/1993 Kahn et al.
5,261,401 A 11/1993 Baker et al.
5,262,943 A 11/1993 Thibado et al.
5,265,888 A 11/1993 Yamamoto et al.
5,266,179 A 11/1993 Nankai et al.
5,275,159 A 1/1994 Griebel
5,282,950 A 2/1994 Dietze et al.
5,295,491 A 3/1994 Gevins
5,299,121 A 3/1994 Brill et al.
5,301,105 A 4/1994 Cummings, Jr.
5,304,112 A 4/1994 Mrklas et al.
5,304,468 A 4/1994 Phillips et al.
5,307,263 A 4/1994 Brown 5,309,919 A 5/1994 Snell et al.
5,321,009 A 6/1994 Baeder et al.
5,325,288 A 6/1994 Satou
5,329,459 A 7/1994 Kaufman et al.
5,329,608 A 7/1994 Bocchieri et al.
5,331,549 A 7/1994 Crawford, Jr.
5,333,981 A 8/1994 Pronovost et al.
5,335,338 A 8/1994 Proesel
5,339,821 A * 8/1994 Fujimoto .................... 600/513
5,341,291 A 8/1994 Roizen et al.
5,343,239 A 8/1994 Lappington et al.
5,344,324 A 9/1994 O'Donnell et al.
5,348,008 A * 9/1994 Bornn et al. ................ 600/301
5,357,427 A 10/1994 Langen et al.
5,366,896 A 11/1994 Margrey et al.
5,368,562 A 11/1994 Blomquist et al.
5,371,687 A 12/1994 Holmes, II et al.
5,375,604 A 12/1994 Kelly et al.
5,377,100 A 12/1994 Pope et al.
5,390,238 A 2/1995 Kirk et al.
5,399,821 A 3/1995 Inagaki et al.
5,410,471 A 4/1995 Alyfuku et al.
5,410,474 A 4/1995 Fox
5,415,167 A * 5/1995 Wilk .......................... 600/407
5,429,140 A 7/1995 Burdea et al.
5,431,690 A 7/1995 Schaldach et al.
5,431,691 A 7/1995 Snell et al.
5,434,611 A 7/1995 Tamura
5,437,278 A * 8/1995 Wilk .......................... 600/425
5,438,607 A 8/1995 Przygoda, Jr. et al.
5,438,983 A 8/1995 Falcone
5,441,047 A 8/1995 David et al.
5,449,334 A 9/1995 Kingsbury
5,454,721 A 10/1995 Kuch
5,454,722 A 10/1995 Holland et al.
5,456,606 A 10/1995 McIntyre
5,456,692 A 10/1995 Smith, Jr. et al.
5,458,123 A 10/1995 Unger
5,467,269 A 11/1995 Flaten
5,471,039 A 11/1995 Irwin, Jr. et al.
5,471,382 A 11/1995 Tallman et al.
5,483,276 A 1/1996 Brooks et al.
5,488,412 A 1/1996 Majeti et al.
5,488,423 A 1/1996 Walkingshaw et al.
5,501,231 A 3/1996 Kaish
5,502,636 A 3/1996 Clarke
5,502,726 A 3/1996 Fischer
5,504,519 A 4/1996 Remillard
5,517,405 A 5/1996 McAndrew et al.
5,518,001 A 5/1996 Snell
5,519,058 A 5/1996 Gonick et al.
5,519,433 A 5/1996 Lappington et al.
5,523,232 A 6/1996 Sechler
5,536,249 A 7/1996 Castellano et al.
5,542,420 A 8/1996 Goldman et al.
5,544,649 A 8/1996 David et al.
5,546,943 A 8/1996 Gould
5,549,117 A 8/1996 Tacklind et al.
5,550,575 A 8/1996 West et al.
5,553,609 A 9/1996 Chen et al.
5,558,638 A 9/1996 Evers et al.
5,564,429 A 10/1996 Bornn et al.
5,569,212 A 10/1996 Brown
5,572,421 A 11/1996 Altman et al.
5,572,646 A 11/1996 Kawai et al.
5,574,828 A 11/1996 Hayward et al.
5,576,952 A 11/1996 Stutman et al.
5,583,758 A 12/1996 McIlroy et al.
5,583,763 A 12/1996 Atcheson et al.
5,590,648 A 1/1997 Mitchell et al.
5,593,349 A 1/1997 Miguel et al.
5,593,390 A 1/1997 Castellano et al.
5,594,637 A 1/1997 Eisenberg et al.
5,596,994 A 1/1997 Bro
5,597,307 A 1/1997 Redford et al.
5,601,435 A 2/1997 Quy
5,613,495 A 3/1997 Mills et al.
5,619,991 A 4/1997 Sloane
5,624,265 A 4/1997 Redford et al.
5,628,309 A 5/1997 Brown
5,629,981 A 5/1997 Nerlikar
5,631,844 A 5/1997 Margrey et al.
5,633,910 A 5/1997 Cohen
5,635,532 A 6/1997 Samid
5,640,569 A 6/1997 Miller et al.
5,640,953 A 6/1997 Bishop et al.
5,642,731 A 7/1997 Kehr
5,642,936 A 7/1997 Evans
5,651,363 A 7/1997 Kaufman et al.
5,651,775 A 7/1997 Walker et al.
5,659,691 A 8/1997 Durward et al.
5,666,487 A 9/1997 Goodman et al.
5,670,711 A 9/1997 Detournay et al.
5,675,635 A 10/1997 Vos et al.
5,678,562 A 10/1997 Sellers
5,678,571 A 10/1997 Brown
5,679,075 A 10/1997 Forrest et al.
5,680,590 A 10/1997 Parti
5,680,866 A 10/1997 Kangas et al.
5,687,322 A 11/1997 Deaton et al.
5,687,717 A 11/1997 Halpern et al.
5,687,734 A 11/1997 Dempsey et al.
5,689,652 A 11/1997 Lupien et al.
5,692,906 A 12/1997 Corder
5,704,364 A 1/1998 Saltzstein et al.
5,704,366 A 1/1998 Tacklind et al.
5,704,902 A 1/1998 Vandenbelt et al.
5,704,922 A 1/1998 Brown
5,710,178 A 1/1998 Samid
5,710,918 A 1/1998 Lagarde et al.
5,711,297 A 1/1998 Iliff
5,714,319 A 2/1998 Joutel et al.
5,715,451 A 2/1998 Marlin
5,715,823 A 2/1998 Wood et al.
5,717,739 A 2/1998 Dyer et al.
5,717,913 A 2/1998 Driscoll
5,720,733 A 2/1998 Brown
5,722,418 A 3/1998 Bro
5,727,153 A 3/1998 Powell
5,730,124 A 3/1998 Yamauchi
5,730,654 A 3/1998 Brown
5,732,696 A 3/1998 Rapoport et al.
5,732,709 A 3/1998 Tacklind et al.
5,734,413 A 3/1998 Lappington et al.
5,749,081 A 5/1998 Whiteis
5,749,083 A 5/1998 Koda et al.
5,752,234 A 5/1998 Withers
5,754,740 A 5/1998 Fukuoka et al.
5,760,771 A 6/1998 Blonder et al.
5,772,585 A 6/1998 Lavin et al.
5,778,882 A 7/1998 Raymond et al.
5,782,814 A 7/1998 Brown et al.
5,785,650 A 7/1998 Akasaka et al.
5,787,295 A 7/1998 Nakao
5,791,342 A 8/1998 Woodard
5,792,117 A 8/1998 Brown
5,793,969 A 8/1998 Kamentsky et al.
5,794,219 A 8/1998 Brown
5,794,251 A 8/1998 Watanabe et al.
5,796,393 A 8/1998 MacNaughton
5,799,318 A 8/1998 Cardinal et al.
5,800,458 A 9/1998 Wingrove
5,802,494 A 9/1998 Kuno
5,802,534 A 9/1998 Hatayama et al.
5,806,057 A 9/1998 Gormley et al.
5,810,747 A 9/1998 Brudny et al.

5,819,735 A 10/1998 Mansfield et al.
5,822,544 A 10/1998 Chaco et al.
5,822,715 A 10/1998 Worthington et al.
5,825,283 A 10/1998 Camhi
5,827,180 A 10/1998 Goodman
5,828,943 A 10/1998 Brown
5,832,446 A 11/1998 Neuhaus
5,832,448 A 11/1998 Brown
5,835,896 A 11/1998 Fisher et al.
5,840,020 A 11/1998 Heinonen et al.
5,842,976 A 12/1998 Williamson
5,868,669 A 2/1999 Iliff
5,868,683 A 2/1999 Protopapas et al.
5,875,432 A 2/1999 Sehr
5,879,163 A 3/1999 Brown et al.
5,882,338 A 3/1999 Gray
5,884,282 A 3/1999 Robinson
5,887,133 A 3/1999 Brown et al.
5,893,077 A 4/1999 Griffin
5,893,098 A 4/1999 Peters et al.
5,897,493 A 4/1999 Brown
5,899,855 A 5/1999 Brown
5,911,687 A 6/1999 Sato et al.
5,913,310 A 6/1999 Brown
5,918,603 A 7/1999 Brown
5,920,477 A 7/1999 Hofbert et al.
5,933,136 A 8/1999 Brown
5,935,060 A 8/1999 Iliff
5,940,801 A 8/1999 Brown
5,941,829 A 8/1999 Saltzstein et al.
5,945,651 A 8/1999 Chorosinski et al.
5,951,300 A 9/1999 Brown
5,954,641 A 9/1999 Kehr et al.
5,956,501 A 9/1999 Brown
5,960,403 A 9/1999 Brown
5,960,440 A 9/1999 Brenner et al.
5,961,446 A 10/1999 Beller et al.
5,963,948 A 10/1999 Shilcrat
5,966,526 A 10/1999 Yokoi
5,971,855 A 10/1999 Ng
5,971,922 A 10/1999 Arita et al.
5,978,766 A 11/1999 Luciw
5,979,757 A 11/1999 Tracy et al.
5,983,003 A 11/1999 Lection et al.
5,983,217 A 11/1999 Khosravi-Sichani et al.
5,987,471 A 11/1999 Bodine et al.
5,995,969 A 11/1999 Lee et al.
5,997,476 A 12/1999 Brown
5,997,502 A 12/1999 Reilly et al.
5,999,975 A 12/1999 Kittaka et al.
6,001,065 A 12/1999 DeVito
6,012,051 A 1/2000 Sammon, Jr. et al.
6,018,738 A 1/2000 Breese et al.
6,020,883 A 2/2000 Herz et al.
6,022,315 A 2/2000 Iliff
6,022,615 A 2/2000 Rettenbacher
6,023,686 A 2/2000 Brown
6,024,281 A 2/2000 Shepley
6,029,138 A 2/2000 Khorasani et al.
6,032,119 A 2/2000 Brown et al.
6,035,328 A 3/2000 Soukal
6,046,021 A 4/2000 Bochner
6,046,761 A 4/2000 Echerer
6,049,794 A 4/2000 Jacobs et al.
6,050,940 A 4/2000 Braun et al.
6,055,314 A 4/2000 Spies et al.
6,055,487 A 4/2000 Margery et al.
6,055,506 A 4/2000 Frasca, Jr.
6,057,758 A 5/2000 Dempsey et al.
6,068,615 A 5/2000 Brown et al.
6,095,985 A 8/2000 Raymond et al.
6,101,478 A 8/2000 Brown
6,110,148 A 8/2000 Brown et al.
6,113,578 A 9/2000 Brown
6,138,145 A 10/2000 Kawanaka
6,144,837 A 11/2000 Quy
6,151,586 A 11/2000 Brown
6,161,095 A 12/2000 Brown
6,167,362 A 12/2000 Brown et al.
6,167,386 A 12/2000 Brown
6,168,563 B1 1/2001 Brown
6,177,940 B1 1/2001 Bond et al.
6,186,145 B1 2/2001 Brown
6,189,029 B1 2/2001 Fuerst
D439,242 S 3/2001 Brown et al.
6,210,272 B1 4/2001 Brown
6,221,012 B1 4/2001 Maschke et al.
6,233,539 B1 5/2001 Brown
6,240,393 B1 5/2001 Brown
6,248,065 B1 6/2001 Brown
6,260,022 B1 7/2001 Brown
6,270,455 B1 8/2001 Brown
6,270,456 B1 8/2001 Iliff
6,334,778 B1 1/2002 Brown
6,352,523 B1 3/2002 Brown et al.
6,368,273 B1 4/2002 Brown
6,370,513 B1 4/2002 Kolawa et al.
6,375,469 B1 4/2002 Brown
6,379,301 B1 4/2002 Worthington et al.
6,381,577 B1 4/2002 Brown
6,436,036 B1 8/2002 Miller-Kovach et al.
6,513,532 B2 2/2003 Mault et al.
2002/0019748 A1 2/2002 Brown
2004/0106855 A1 6/2004 Brown
2004/0107116 A1 6/2004 Brown
2004/0117207 A1 6/2004 Brown
2004/0117208 A1 6/2004 Brown
2004/0117209 A1 6/2004 Brown
2004/0117210 A1 6/2004 Brown
2005/0080652 A1* 4/2005 Brown .......................... 705/2
2005/0086083 A1* 4/2005 Brown .......................... 705/2
2005/0256739 A1* 11/2005 Brown .......................... 705/2

FOREIGN PATENT DOCUMENTS

EP 0320749 6/1989
EP 370599 5/1990
EP 0461910 12/1991
EP 508912 10/1992
EP 526166 2/1993
EP 0558975 9/1993
EP 0653718 5/1995
EP 676709 10/1995
EP 680727 11/1995
EP 761160 3/1997
EP 08131551 12/1997
EP 0251520 1/1998
GB 2218831 11/1989
GB 2225637 6/1990
JP 54005785 1/1979
JP 54146633 11/1979
JP 62226278 10/1987
JP 5155024 6/1993
JP 5266002 10/1993
JP 1995407095963 4/1995
JP 08063455 3/1996
JP 408064355 3/1996
WO WO-8501667 4/1985
WO WO-90/00367 1/1990
WO WO-9109374 6/1991
WO WO-93/01489 1/1993
WO WO-9302622 2/1993
WO WO-9416774 8/1994
WO WO-95/09386 4/1995
WO WO-95/20199 7/1995
WO WO-9522131 8/1995

| | | |
|---|---|---|
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9831275 | 7/1998 |
| WO | WO-9839933 | 9/1998 |

OTHER PUBLICATIONS

Bill Communications Inc. A Steady Stream of New Applications . . . Institutional Distribution v19. Nov. 1983.

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

Jaffrey et al.; "PIN: An Assocaited Protein Inhibitor of Neuronal Nitric Oxide Synthase"; Science; vol. 274; Nov. 1, 1996; Ref: XP 002050141.

"Blood Glucose Monitors", Portable Health Device, (1998), vol. 17(9), pp. 253-271.

"Talking Nano Puppy"; retrieved from URL http://www.virtualpet.com/vp/farm/nano/talkn/talkn.htm Apr. 23, 2000.

Voelker, Rebecca, "Shoe Leather Therapy is Gaining on TB", Jama, (Mar. 13, 1996), vol. 275, 743.

"Digital Doggie"; retrieved from URL http:www.virtualpet.com/vp/farm/gigapet/ddoggie.htm Apr. 23, 2000.

ANONYMOUS, "Health Hero Network, Inc. Receives First-Ever FDA Clearance for Connecting Medical Devices to Internet", PR Newswire, (Dec. 2, 1993), 3 pages.

"Playmates Toys deals knockout blow to virtual pet competitors with introduction of Nano Fighter™ For Boys"; New Nano Pet Fighting Pet Press Release; retrieved from URL http://www.virtualpet.com/vp/farm/nano/nfightpr.htm Apr. 23, 2000.

Updike, Stuart J., et al., "Laboratory Evaluation of New Reusable Blood Glucose Sensor", Diabetes Care, (Nov./Dec. 1998), vol. 11, No. 10, pp. 801-807.

RO_AUCTION Auctioneers Property Database System and RO_AUCTION Auctioneers Accounting System; RO-AUCTION features; Dec. 4, 1995.

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Reis, H, "Telemedicine: Transmitting Expertise to the Point of Care Toward an Electronic Patient Record"; '97, Nashville, TN, Apr. 27-May 3, 1997, pp. 248-256, v. 3.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

United Healthcare's OPTUM Division goes online to better health by announcing a unique internet application. PR Newswire, p0801MNTH004. Aug. 1, 1996.

Hunter, "Technological Advances in Bedside Monitoring: Biosensors", Archives and Laboratory Medicine, (Jul. 1987), pp. 633-636.

Telemedicine Provides Two-Way Computer Link For Parents of Very Premature Infants. PR Newswire. p1007NEM034. Oct. 7, 1996.

Schrezenmeir, J. et al., "Computer Assisted Insulin Dosage Adjustment—Perspective for Diabetes Control", Hormone and Metabolic Research, Supplement Series, (1990), vol. 24, pp. 116-123.

Save the earth artrock auction, http://www.commerce.com.save-earth. Auction Web, http://www.ebay.com.

Makikawa, M., et al., "Microprocessor-Based Memory Device for Ambulatory Heart Rate and and Physical Activity Recording", Methods of Information in Medicine, (1994), vol. 33, No. 1, pp. 94-96.

Luebke, Cathy, "Barrett-Jackson Auction Turns High-Tech", Business Journal, vol. 16, Issue 12, pp. 11, Jan. 19, 1996.

Schenkels, P., "Supplementary European Search Report", Application No. EP 97 92 2716, (Mar. 11, 2002).

"Theme Hospital," product review 1996 [retrieved Apr. 21, 2000], Retrieved from <URL:www.vigilante.co.uk/ep/misc/hospital.htm>.

Potter, David, "Fundamentals of PC-Based Data Acquisition", SENSORS, (Feb. 1994), pp. 12-20.

"Virtual Tomagutchi,"1998 [retrieved Apr. 23, 2000], Retrieved from <URL:www.sttf.org/english/action/tomagutchi.html>.

Roberts; "Diabetes and Stress: A Type A Connection?", Psychology Today, (Jul. 1987), v. 21; pp. 22(1); Dialog: File 149, Acc# 05038381.

"Virtual Pet Product Reviews," 1997 [retrieved on Apr. 23, 2000], Retrieved from <URL:www.virtualpet.com/vp/farm/reviews/reviews,htm>.

Soeldner, J. S., "Treatment of Diabetes Mellitus by Devices", The American Journal of Medicine, (Jan. 1981), vol. 70, 183-194.

"Giga Pets," 1997 [retrieved on Apr. 23, 2000], Retrieved from <URL:www.virtualpet.com/vp/farm/gigapet/gigapet.htm>.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Franklin; "Proposed Auction Rules for PCS: The FCC Plans to Use Competitive Bidding, but Exact Procedures are Undefined"; Cellular Business; v10 n13; p. 18(2); Dec. 1993; DIALOG: File 148, Acc#06787310.

"Towards a partnership of care", M2 Presswire, Jun. 14, 2000.

Moore, "New Applications Break Through Storage Boundaries", Computer Technology Review, (Oct. 1999), vol. 19, No. 10 p. 1.

"Who Will Dominate The Desktop in the 90's?", Jack Shandle, Electronics, Feb. 1990, pp. 48-50. (3 pages) Cited by 2 patents.

Howey, et al., "A Rapidly Absorbed Analogue of Human Insulin"; Diabetes, vol. 43, Mar. 1994, pp. 396-402. (7 pages).

Jimison et al., "Patient-Specific explanation in models of chronic disease", Revised Feb. 1992 Artificial Intelligence in Medicine 4 (1992) 191-205.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 01624462.

Jones, Chris, "Microsoft readies DocObject; technology will allow document editing in Web browsers", InfoWorld, v18 n18 p. 48(1), Apr. 29, 1996.

"AdOptimizer—Ad Management Software For Websites", Newsbytes, pNew10040041, Oct. 4, 1996.

"New Horizons teams with Duke, Real Media"; The Seybold Report on Desktop Publishing, v10 n12 p. 24(1), Aug. 12, 1996.

Marsh, David G. "Approaches Toward the Genetic Analysis of Complex Traits Asthma and Atrophy", Am. J. Respir.Crit.Care Med., (1997), vol. 156, pp. S-133-S138.

Mims; "Psychological Testing"; Computers & Electronics; v23; p. 22(6); Feb. 1985; Dialog: File 47, Acc# 2654858.

Wilkins, Aaron. "Expanding Internet access for health care consumers", Health Care Management Review, Summer, Jul. 1999, 24-30.

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Leyerle, Beverly J., et al., "PDMS as a Focal Point for Distributed Patient Data", International Journal of Clinical Monitoring and Computing, (1988), vol. 5, pp. 155-161.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Octogotchi Instruction Manual, 1997. Dino-Kun Instruction Manual, 1997.

Gardner, et al.; "Comprehension and Appreciation of Humorous Material Following Brain Damage"; Brain; Sep. 1975; 98(3); pp. 399-412; Dialog: File 153, Acc#02859983. (14 pages).
Latman, N.S., "Evaluation of Electronic, Digital Blood Glucose Monitors", Biomedical Instrumentation and Technology, (1991), vol. 25, No. 1, 43-49.
Edelson; "Fashion Reevaluates Flickering Fortunes of TV Home Shopping"; WWD; v170 n87; p. 1(3); Nov. 8, 1995; DIALOG: File 148, Acc#08289119.
Results of the world's first on-line auction, http://www.christies.com.
"Cathay Pacific Airways-USA to Hold First-Ever Internet CyberAuction; CyberTravelers Can Bid for 50 Business Class Round Trips to Hong Kong—No Minimum Bid"; Business Wire; p. 9261084; Sep. 26, 1995; DIALOG: File 148, Acc#08167091.
Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.
"ONSALE Onsale Brings Thrill of Auctions and Bargain Hunting Online; Unique Internet retail service debuts with week-long charity auction for The Computer Museum in Boston", May 24, 1995; Dialog Abstract: File 610, Acc#0489267.
"Playmates Toys leads Americas virtual pet craze into its next generation by introducting talking Nano Pals"; Talking Nano Pet Press Release; Nov. 18, 1997; retrieved from URL http://www.virtualpet.com/vp/farm/nano/talkn/tnpress.htm on Apr. 23, 2000.
O'Donnell; "Alan's At It Again"; Bond Buyer; v309 n29448; p. 1(3); Jul. 21, 1994; DIALOG: File 148, Acc#07478152.
Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.
Gauntlet (for PC) rulebook by Mindscape Inc. (Gauntlet by Apple); 1985.
Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996, Ref: XP-002104701.
Bai, "Design of home healthcare network", IEEE 1997 pp. 1657-1658.
Horio, Hiroyuki, et al., "Clinical Telecommunication Network System for Home Monitoring", Medical & Biological Engineering & Computing, (Mar. 1994), vol. 32, 227-230.
"The description of the Tandy Radio Shack TRS-80 Model 100/102 device available at http://www.old-computuers.com/musuem/computer.asp?c=233 ", World Wide Web, (Feb. 13, 2004), 1-3.
Brunetti, P., et al., "A Simulation Study on a Self-Turning Portable Controller of Blood Glucose", The International Journal of Artificial Organs, (1993), vol. 16, No. 16, pp. 51-57.
Cheng, Joe H., "PCT Search Report", (Jan 11, 1996).
Hauben, Jay R., "A Brief History of the Cleveland Free-Net", available at http://www.ais.org/~irh/acn7-1.a09.html, (1995) pp. 1-4.
Hauser, et al., "Will Computers Replace or Complement the Diabetes Educator?", The Medical Journal of Austrailia, (Oct. 5, 1992), vol. 157, 489-491.
Lacyk, John, "PCT Search Report", (Jun. 12, 1997).
Miles, Laughton E., "A Portable Microcomputer for Long-Term Physiological Monitoring in the Home and Work Environment", Medical Monitoring in the Home and Work Environment, (1990), pp. 47-57.
Giuffrida, et al., Should We Pay the Patient? Review of Financial Incentives to enhance Patient Compliance:, Biomedical Journal, (1997), vol. 315, pp. 703-707.
Pfeiffer, E. F., "The Glucose Sensor: The Missing Link in Diabetes Therapy", Hormone and Metabolic Research, (1990), vol. 24m Suppl. pp. 154-164.
Schork, Nicholas J., "Genetics of Complex Disease", Am.J.Respir. Crit. Care Me., (1997), vol. 156, pp. S103-S109.
Shandle, Jack, "Who will dominate the desktop In the 90's?", Electronics, (Feb. 1990), pp. 48-50.
FINSTON, "Parent + Teacher = Healthy Child", Diabetes Forecast, (Apr. 1994), v47 n9; p. 26(5); Dialog: file 149, Acc# 15804228.
M.U.L.E. rulebook by Electronic Arts, 1983.
"Onsale Joins Fray as Online Shopping Picks Up Speed: Internet Booms"; Computer Reseller News; Jun. 5, 1995; p. 73; DIALOG: File 16, Acc#05649796.
Siegmann;"Nowhere to Go but Up"; PC Week; v12 n42, p. A5(1); Oct. 23, 1995; DIALOG: File 148, Acc#08222496.
Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.
Adilman; "Videogames: Knowing the Score"; Creative Computing; v9; p. 224(5); Dec. 1983; Dialog: File 148, Acc#01891055.
Marx, Wendy, "More than just the Scores: ESPNET SportsZone is a model for expanding brand names online", InformationWeek, n576 p. 61(2), Apr. 22, 1996.
Skolnick et al. "Simultaneous Analysis of Multiple Polymorphic Loci Using Amplified Sequence Polymorphisms (ASPs)"; Genomics. 2: 273-279.
Caprihan, A., et al., "A Simple Microcomputer for Biomedical Signal Processing", IECI '78 Annual Conference Proceedings on Industrial Applications of Microprocessors, (Mar. 20, 1978), 18-23.
"Tamagotchi," 1997 [retrieved on Apr. 23, 2000], Retrieved from <URL:www.virtualpet.com/vp/farm/lleg/lleg.htm>.
"Putting the Lot on the Net", Antique Collector, vol. 66, Issue 9, p. 26, Downloaded from Corporate Resource Net, Nov./Dec. 1995.
Lachnit, Carroll, "Hawkin'Online Auction", Photo District News, vol. 16, Issue 1, p. 18, Jan. 1996.
Bruce, "Health Hero Network CEO, CNNfn", Digital Jam, (Dec. 1, 1999), 3.
"Cathay Pacific Airways-USA receives more than 1,300 bids during first five days of CyberAuction"; Business Wire, Oct. 18, 1995, p. 10181119.
"Nano Fighter Pets"; retrieved from URL http://www.virtualpet.com/vp/farm/nano/nfighter.htm Apr. 23, 2000.
"Giga Farm"; retrieved from URL http://www.virtualpet.com/vp/farm/gigapet/gpfarm/gpfarm.htm Apr. 23, 2000.
Billiard, A., et al. "Telematic Transmission of Computerized Blood Glucose Profiles for IDDm Patients", Diabetes Care, (Feb. 1991), vol. 14, No. 2, pp. 130-134.
Bower, "Brain Clues to Energy-efficient Learning", Science News, (Apr. 1992), v. 141; p. 215(1); Dialog: File 647, Acct# 12123949.
Frieberger, Paul, "Video Game Takes on Diabetes Superhero 'Captain Novolin' Offers Treatment Tips", San Francisco Examiner, (Jun. 26, 1992), Fourth Edition, Business Section B1.
Kaufman, Steven, B., "The Learning Game", Nation's Business, (Nov. 1993).
Albisser, A.M. "Intelligent Instrumentation in Diabetic Management", CRC Critical Reviews in Biomedical Engineering, vol. 17, No. 1, pp. 1-24.
Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.
Wyatt, J. C., "Clinical Data Systems, Part 2: Components and Techniques", Lancet, (Dec. 1994), vol. 344, No. 8937, pp. 1609-1614.
Gordon; "Auctions Become High Tech"; Dealer Business; v29 n7; p. 21(4); Mar. 1995; DIALOG: File 148, Acc#07862519.
"Introducing the Next Generation of About Your Diabetes", U.S. Pharmacopical Convention and American Diabetes Association, (1993).
Hutheesing, Nikhil, "An on-line gamble", Forbes, v157 n10 p. 288(1), May 20, 1996.
"Future of the Virtual Pet Industry," 1997 [retrieved on Apr. 23, 2000], Retrieved from <URL:www.virtualpet.com/vp/ future/future.htm>.
DigiPet Instruction Manual, 1997.
"European Search Report", From 6858P005EP, (Mar. 27, 1998).
"Nano Baby Instructions"; retrieved from file://C:\My Documents\Nano Baby Instructions.htm Apr. 23, 2000.

"How Flash Memory Works", Internet printout of URL address: http://www.howstuffworks.com/flash-memory4.htm, (Sep. 28, 2002), 2 pages.

Fox, "Not My Type: Type B Behavior, Type I Diabetes Plus Stress Equals Blood Sugar Blues", Health, (Mar. 1998), v20 n3; pp. 22(1); Dialog; File 149, Acc# 06397959.

"CD-ROM Mavericks: Proprietary TV-Based Players", Byte Guide to CD-ROM, pp. 100-105.

Vallera, D. A., et al., "Accuracy of Portable Blood Glucose Monitoring", American Journal of Clinical Pathology, (1991), vol. 95, No. 2, pp. 247-252.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Nano Page, 1997 [retrieved on Apr. 23, 2000], Retrieved from <URL:www.virtualpet.com/vp/farm/nano/nano.htm>.

"+5V Powered Isolated RS-232 Drivers/Receivers" Maxim Integrated Products.

"Central Fetal Monitoring Systems with Optical Disk Storage", New Technology Brief, (Nov./Dec. 1998), vol. 2, No. 6, pp. 249-251.

Meissner, et al., "Building an Integrated Clinical and Research Network", Proceedings of the SPIE, (Oct. 24, 1995), vol. 2681, p. 92-99.

Bruce, et al., "The Effects of Sympathetic Nervous System Activation and Psychological Stress . . . ", Diabetologia; 35(9); 1992; 835-843; Dialog: File 5, Acc#9629427. (9 pages).

Schement, "An Intelligent Controller for Neurophysiological Experiments," Proceeding of the Annual Symposium on Computer Based Medical Systems, Durham, Jun. 14-17, 1992, p. 528, line 1—page 529, line 21.

Martinez, Fernando D., "Complexities of the Genetics of Asthma", Am.J. Respir. Crit. Care Med., (1997), vol. 156, pp. S117-S122.

Spitzer et al.; "The moderating effect of age on self-care"; Western Journal Of Nursing Research, v18, n2, p. 136(13), Apr. 1996.

Research project launched to improve health of America's communities; new Disney community in Florida is focus of program. Business Wire, p. 10011142. Oct. 1, 1996.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

* cited by examiner

Attention

Calibration was not successful.

Please insert the code strip again.

June 19 12:30 pm

Blood Glucose 109 mg /dl remove test strip

Mon Sept. 28 1992

Sept. 20-26 1992

Glucose
Ave: 123 mg/dl
SD: 56
Num: 15
No. under 50: 13
No. hypo sym: 23

June 12 9:30pm
BG 113 mg/dl
Regin 12.5 U
NPHin 13.2 U
Food 1 BE
Pre-meal HYPO 16
18
52
50
110
14
112
100
106
42
104
108
102

SYSTEM AND METHOD FOR MONITORING USER-RELATED DATA FROM A PERSON

CROSS REFERENCE TO RELATED APPLICATIONS

This application is a divisional of application Ser. No. 10/605,547 filed on Oct. 7, 2003, currently pending, which is a Continuation of application Ser. No. 09/237,194, filed on Jan. 26, 1999, currently pending, which is a Continuation of application Ser. No. 08/481,925, filed on Jun. 7, 1995, now U.S. Pat. No. 5,899,855, which is a Continuation of application Ser. No. 08/233,397, filed on Apr. 26, 1994, now abandoned, which is a Continuation-in-Part of application Ser. No. 07/977,323, filed Nov. 11, 1992, now U.S. Pat. No. 5,307,263. The contents of these applications are incorporated by reference herein, in their entirety.

BACKGROUND OF INVENTION

Controlling or curing conditions of ill health generally involves both establishing a therapeutic program and monitoring the progress of the afflicted person. Based on that progress, decisions can be made as to altering therapy to achieve a cure or maintain the affliction or condition at a controlled level. Successfully treating certain health conditions calls for rather frequent monitoring and a relatively high degree of patient participation. For example, in order to establish and maintain a regimen for successful diabetes care, a diabetic should monitor his or her blood glucose level and record that information along with the date and time at which the monitoring took place. Since diet, exercise, and medication all affect blood glucose levels, a diabetic often must record data relating to those items of information along with blood glucose level so that the diabetic may more closely monitor his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including arrangements for self-care monitoring of various chronic conditions. With respect to the control and monitoring of diabetes, relatively inexpensive and relatively easy-to-use blood glucose monitoring systems have become available that provide reliable information that allows a diabetic and his or her healthcare professional to establish, monitor and adjust a treatment plan (diet, exercise, and medication). More specifically, microprocessor-based blood glucose monitoring systems are being marketed which sense the glucose level of a blood sample that is applied to a reagent-impregnated region of a test strip that is inserted in the glucose monitor. When the monitoring sequence is complete, the blood glucose level is displayed by, for example, a liquid crystal display (LCD) unit.

Typically, currently available self-care blood glucose monitoring units include a calendar/clock circuit and a memory circuit that allows a number of blood glucose test results to be stored along with the date and time at which the monitoring occurred. The stored test results (blood glucose level and associated time and date) can be sequentially recalled for review by the blood glucose monitor user or a health professional by sequentially actuating a push button or other control provided on the monitor. In some commercially available devices, the average of the blood glucose results that are stored in the monitor (or the average of the results for a predetermined period of time, e.g., fourteen days) also is displayed during the recall sequence. Further, some self-care blood glucose monitors allow the user to tag the test result with an "event code" that can be used to organize the test results into categories. For example, a user might use a specific event code to identify test results obtained at particular times of the day, a different event code to identify a blood glucose reading obtained after a period of exercise, two additional event codes to identify blood glucose readings taken during hypoglycemia symptoms and hyperglycemia symptoms, etc. When event codes are provided and used, the event code typically is displayed with each recalled blood glucose test result.

Microprocessor-based blood glucose monitoring systems have advantages other than the capability of obtaining reliable blood glucose test results and storing a number of the results for later recall and review. By using low power microprocessor and memory circuits and powering the units with small, high capacity batteries (e.g., a single alkaline battery), extremely compact and light designs have been achieved that allow taking the blood glucose monitoring system to work, school, or anywhere else the user might go with people encountered by the user not becoming aware of the monitoring system. In addition, most microprocessor-based self-care blood glucose monitoring systems have a memory capacity that allows the system to be programmed by the manufacturer so that the monitor displays a sequence of instructions during any necessary calibration or system tests and during the blood glucose test sequence itself. In addition, the system monitors various system conditions during a blood glucose test (e.g., whether a test strip is properly inserted in the monitor and whether a sufficient amount of blood has been applied to the reagent impregnated portion of the strip) and if an error is detected generates an appropriate display (e.g., "retest"). A data port may be provided that allows test results stored in the memory of the microprocessor-based blood glucose monitoring system to be transferred to a data port (e.g., RS-232 connection) of a personal computer or other such device for subsequent analysis.

Microprocessor-based blood glucose monitoring systems are a significant advance over previously available self-care systems such as those requiring a diabetic to apply a blood sample to reagent activated portions of a test strip; wipe the blood sample from the test strip after a predetermined period of time; and, after a second predetermined period of time, determine blood glucose level by comparing the color of the reagent activated regions of the test strip with a color chart supplied by the test strip manufacturer. Despite what has been achieved, numerous drawbacks and disadvantages still exist. For example, establishing and maintaining diabetic healthcare often requires the diabetic to record additional data pertaining to medication, food intake, and exercise. However, the event codes of currently available microprocessor blood glucose monitoring systems provide only limited capability for tagging and tracking blood glucose test results according to food intake and other relevant factors. For example, the event codes of currently available monitoring systems only allow the user to classify stored blood glucose readings in a manner that indicates blood glucose tests taken immediately after a heavy, light or normal meal. This method of recording information not only requires subjective judgment by the system user, but will not suffice in a situation in which successfully controlling the user's diabetes requires the recording and tracking of relatively accurate information relating to food intake, exercise, or medication (e.g., insulin dosage). An otherwise significant advantage of currently available blood glucose monitoring systems is lost when blood glucose test results must be recorded and tracked with quantitative information relating to medication, food intake, or exercise. Specifically, the system user must record the required information along with a time and date tagged blood glucose test result by, for example, writing the information in a log book.

The use of event codes to establish subcategories of blood glucose test results has an additional disadvantage or drawback. In particular, although alphanumeric display devices are typically used in currently available microprocessor-based blood glucose monitoring systems, the display units are limited to a single line of information having on the order of six characters. Moreover, since the systems include no provision for the user to enter alphanumeric information, any event codes that are used must be indicated on the display in a generic manner, e.g., displayed as "EVENT 1", EVENT 2" etc. This limitation makes the system more difficult to use because the diabetic must either memorize his or her assignment of event codes or maintain a list that defines the event codes. The limited amount of data that can be displayed at any one time presents additional drawbacks and disadvantages. First, instructions and diagnostics that are displayed to the user when calibrating the system and using the system to obtain a blood glucose reading must be displayed a line at a time and in many cases, the information must be displayed in a cryptic manner.

The above-discussed display limitations and other aspects of currently available blood glucose monitoring systems is disadvantageous in yet another way. Little statistical information can be made available to the user. For example, in diabetic healthcare maintenance, changes or fluctuations that occur in blood glucose levels during a day, a week, or longer period can provide valuable information to a diabetic and/or his or her healthcare professional. As previously mentioned, currently available systems do not allow associating blood glucose test results with attendant quantitative information relating to medication, food intake, or other factors such as exercise that affect a person's blood glucose level at any particular point in time. Thus, currently available blood glucose monitoring systems have little or no capability for the generating and display of trend information that may be of significant value to a diabetic or the diabetic's healthcare professional.

Some currently available blood glucose monitoring systems provide a data port that can be interconnected with and transfer data to a personal computer (e.g., via an RS-232 connection). With such a system and a suitable programmed computer, the user can generate and display trend information or other data that may be useful in administering his or her treatment plan. Moreover, in such systems, data also can be transferred from the blood glucose monitoring system to a healthcare professional's computer either directly or remotely by telephone if both the blood glucose monitoring system (or computer) to which the data has been downloaded and the healthcare professional's computer are equipped with modems. Although such a data transfer provision allows a healthcare professional to analyze blood glucose data collected by a diabetic, this aspect of currently available blood glucose monitoring systems has not found widespread application. First, the downloading and subsequent analysis feature can only be used by system users that have ready access to a computer that is programmed with appropriate software and, in addition, have both the knowledge required to use the software (and the inclination to do so). This same problem exists with respect to data transfer to (and subsequent analysis by) a healthcare professional. Moreover, various manufacturers of systems that currently provide a data transfer feature do not use the same data format. Therefore, if a healthcare professional wishes to analyze data supplied by a number of different blood glucose monitoring systems, he or she must possess software for each of the systems and must learn to conduct the desired analyses with each software system.

The above-discussed disadvantages and drawbacks of microprocessor-based self-care health monitoring systems take on even greater significance with respect to children afflicted with diabetes, asthma and other chronic illnesses. In particular, a child's need for medication and other therapy changes as the child grows. Current microprocessor-based self-care health monitoring systems generally do not provide information that is timely and complete enough for a healthcare professional to recognize and avert problems before relatively severe symptoms develop. Too often, a need for a change in medication and/or other changes in therapeutic regimen is not detected until the child's condition worsens to the point that emergency room care is required.

Further, currently available microprocessor-based health monitoring systems have not been designed with children in mind. As previously mentioned, such devices are not configured for sufficient ease of use in situations in which it is desirable or necessary to record and track quantitative information that affects the physical condition of the system user (e.g., medication dosage administered by a diabetic and food intake). Children above the age at which they are generally capable of obtaining blood samples and administering insulin or other medication generally can learn to use at least the basic blood glucose monitoring features of currently available microprocessor-based blood glucose monitoring systems. However, the currently available monitoring systems provide nothing in the way of motivation for a child to use the device and, in addition, include little or nothing that educates the child about his or her condition or treatment progress.

The lack of provision for the entering of alphanumeric data also can be a disadvantage. For example, currently available blood glucose monitoring systems do not allow the user or the healthcare professional to enter information into the system such as medication dosage and other instructions or data that is relevant to the user's self-care health program.

The above-discussed disadvantages and drawbacks of currently available microprocessor-based blood glucose monitoring systems also have been impediments to adopting the basic technology of the system for other healthcare situations in which establishing and maintaining an effective regimen for cure or control is dependent upon (or at least facilitated by) periodically monitoring a condition and recording that condition along with time and date tags and other information necessary or helpful in establishing and maintaining a healthcare program.

SUMMARY OF INVENTION

This invention provides a new and useful system for healthcare maintenance in which the invention either serves as a peripheral device to (or incorporates) a small handheld microprocessor-based unit of the type that includes a display screen, buttons or keys that allow a user to control the operation of the device and a program cartridge or other arrangement that can be inserted in the device to adapt the device to a particular application or function. The invention in effect converts the handheld microprocessor device into a healthcare monitoring system that has significant advantages over systems such as the currently available blood glucose monitoring systems. To perform this conversion, the invention includes a microprocessor-based healthcare data management unit, a program cartridge and a monitoring unit. When inserted in the handheld microprocessor unit, the program cartridge provides the software necessary (program instructions) to program the handheld microprocessor unit for operation with the microprocessor-based data management unit. Signal communication between the data management unit and the handheld microprocessor unit is established by an interface cable. A second interface cable can be used to establish signal communication between the data management unit and the monitoring unit or, alternatively, the monitoring unit can be constructed as a plug-in unit having an electrical connector that mates with a connector mounted within a region that is configured for receiving the monitoring unit.

In operation, the control buttons or keys of the handheld microprocessor-based unit are used to select the operating mode for both the data management unit and the handheld microprocessor-based unit. In response to signals generated by the control buttons or keys, the data management unit generates signals that are coupled to the handheld microprocessor unit and, under control of the program instructions contained in the program cartridge, establish an appropriate screen display on the handheld microprocessor-based unit display. In selecting system operating mode and other operations, the control buttons are used to position a cursor or other indicator in a manner that allows the system user to easily select a desired operating mode or function and provide any other required operator input. In the disclosed detailed embodiment of the invention several modes of operation are made available.

In the currently preferred embodiments of the invention, the handheld microprocessor unit is a compact video game system such as the system manufactured by Nintendo of America Inc. under the trademark “GAME BOY.” Use of a compact video game system has several general advantages, including the widespread availability and low cost of such systems. Further, such systems include switch arrangements that are easily adapted for use in the invention and the display units of such systems are of a size and resolution that can advantageously be employed in the practice of the invention. In addition, such systems allow educational or motivational material to be displayed to the system user, with the material being included in the program cartridge that provides the monitor system software or, alternatively, in a separate program cartridge.

The use of a compact video game system for the handheld microprocessor-based unit of the invention is especially advantageous with respect to children. Specifically, the compact video game systems of the type that can be employed in the practice of the invention are well known and well accepted by children. Such devices are easily operated by a child and most children are well accustomed to using the devices in the context of playing video games. Motivational and educational material relating to the use of the invention can be presented in game-like or animated format to further enhance acceptance and use of the invention by children that require self-care health monitoring.

A microprocessor-based health monitoring system that is configured in accordance with the invention provides additional advantages for both the user and a healthcare professional. In accordance with one aspect of the invention, standardized reports are provided to a physician or other healthcare provider by means of facsimile transmission. To accomplish this, the data management unit of the currently preferred embodiments of the invention include a modem which allows test results and other data stored in system memory to be transmitted to a remote clearinghouse via a telephone connection. Data processing arrangements included in the clearinghouse perform any required additional data processing; format the standardized reports; and, transmit the reports to the facsimile machine of the appropriate healthcare professional.

The clearinghouse also can fill an additional communication need, allowing information such as changes in medication dosage or other information such as modification in the user’s monitoring schedule to be electronically sent to a system user. In arrangements that incorporate this particular aspect of the invention, information can be sent to the user via a telephone connection and the data management unit modem when a specific inquiry is initiated by the user, or when the user establishes a telephone connection with the clearinghouse for other purposes such as providing data for standardized reports.

The clearinghouse-facsimile aspect of the invention is important because it allows a healthcare professional to receive timely information about patient condition and progress without requiring a visit by the patient (system user) and without requiring analysis or processing of test data by the healthcare professional. In this regard, the healthcare professional need not possess or even know how to use a computer and/or the software conventionally employed for analysis of blood glucose and other health monitoring data and information.

The invention also includes provision for data analysis and memory storage of information provided by the user and/or the healthcare professional. In particular, the data management units of the currently preferred embodiments of the invention include a data port such as an RS-232 connection that allows the system user or healthcare professional to establish signal communication between the data management unit and a personal computer or other data processing arrangement. Blood glucose test data or other information can then be downloaded for analysis and record keeping purposes. Alternatively, information such as changes in the user’s treatment and monitoring regimen can be entered into system memory. Moreover, if desired, remote communication between the data management unit and the healthcare professional’s computer can be established using the clearinghouse as an element of the communications link. That is, in the currently preferred arrangements of the invention a healthcare professional has the option of using a personal computer that communicates with the clearinghouse via a modem and telephone line for purposes of transmitting instructions and information to a selected user of the system and/or obtaining user test data and information for subsequent analysis.

The invention can be embodied in forms other than those described above. For example, although small handheld microprocessor units such as a handheld video game system or handheld microprocessor units of the type often referred to as “palm-computers provide many advantages, there are situations in which other compact microprocessor units can advantageously be used. Among the various types of units that can be employed are using compact video game systems of the type that employ a program cartridge, but uses a television set or video monitor instead of a display unit that is integrated into the previously described handheld microprocessor units.

Those skilled in the art also will recognize that the above-described microprocessor-implemented functions and operations can be apportioned between one or more microprocessors in a manner that differs from the above-described arrangement. For example, in some situations, the programmable microprocessor unit and the program cartridge used in practicing the invention may provide memory and signal processing capability that is sufficient for practicing the invention. In such situations, the microprocessor of the microprocessor-based data management unit of the above embodiments in effect is moved into the video game system, palm-computer or programmable microprocessor device. In such an arrangement, the data management unit can be realized as a relatively simple interface unit that includes little or no signal processing capability. Depending upon the situation at hand, the interface unit may or may not include a telephone modem and/or an RS-232 connection (or other data port) for interconnecting the healthcare system with a computer or other equipment. In other situations, the functions and operations associated with processing of the monitored health care data may be performed by a microprocessor that is added to or already present in the monitoring device that is used to monitor blood glucose or other condition.

Because the invention can be embodied to establish systems having different levels of complexity, the invention satisfies a wide range of self-care health monitoring applications. The arrangements that include a modem (or other signal transmission facility) and sufficient signal processing capability can be employed in situations in which reports are electronically transmitted to a healthcare professional either in hard copy (facsimile) form or in a signal format that can be received by and stored in the healthcare professional's computer. On the other hand, less complex (and, hence, less costly) embodiments of the invention are available for use in which transfer of system information need not be made by means of telephonic data transfer or other remote transmission methods. In these less complex embodiments, transfer of data to a healthcare professional can still be accomplished. Specifically, if the program cartridge includes a battery and suitable program instructions, monitored healthcare data can be stored in the program cartridge during use of the system as a healthcare monitor. The data cartridge can then be provided to the healthcare professional and inserted in a programmable microprocessor-based unit that is the same as or similar to that which was used in the healthcare monitoring system. The healthcare professional can then review the data, and record it for later use, and/or can use the data in performing various analyses. If desired, the microprocessor-based unit used by the healthcare professional can be programmed and arranged to allow information to be stored in the cartridge for return to and retrieval by the user of the healthcare monitoring system. The stored information can include messages (e.g., instructions for changes in medication dosage) and/or program instructions for reconfiguring the program included in the cartridge so as to effect changes in the treatment regimen, the analyses or reports to be generated by the healthcare monitoring system, or less important aspects such as graphical presentation presented during the operation of the healthcare system.

BRIEF DESCRIPTION OF DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION

Figure 1:
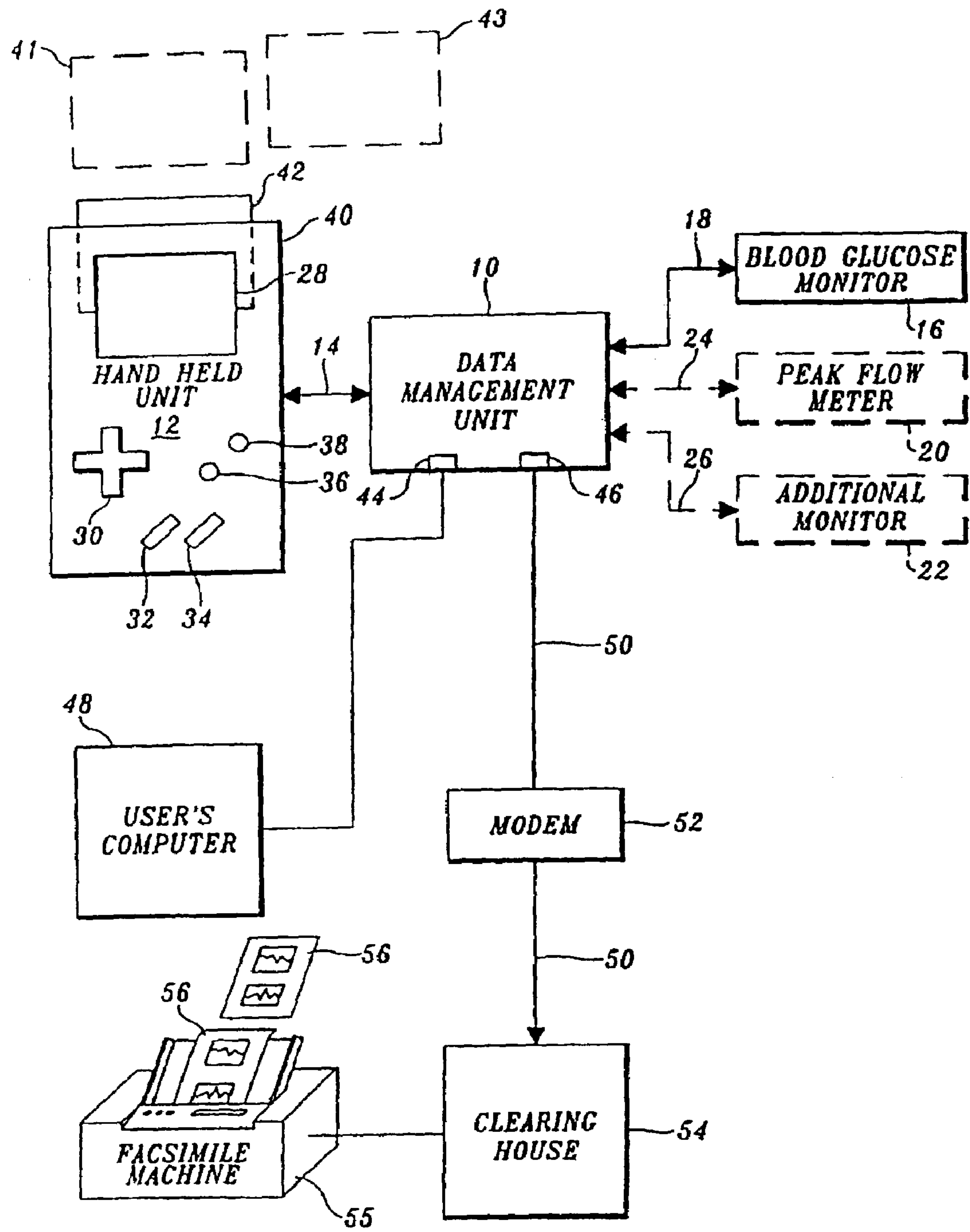
FIG. 1 is a block diagram that illustrates a healthcare monitoring system arranged in accordance with the invention.

FIG. 1 depicts a self-care health monitoring system arranged in accordance with the invention. In the arrangement shown in FIG. 1 a data management unit 10 is electrically interconnected with a handheld microprocessor-based unit 12 via a cable 14. In the depicted arrangement, data management unit 10 also is electrically interconnected with a blood glucose monitor 16 of the type capable of sensing blood glucose level and producing an electrical signal representative thereof. Although FIG. 1 illustrates blood glucose monitor 16 as being connected to data management unit 10 by a cable 18, it may be preferable to construct blood glucose monitor 16 as a plug-in unit that is placed in a recess or other suitable opening or slot in data management unit 10. Regardless of the manner in which blood glucose monitor 16 is interconnected with data management unit 10, both that interconnection and cable 14 are configured for serial data communication between the interconnected devices.

Also shown in FIG. 1 are two additional monitoring devices 20 and 22, which are electrically connected for serial data communication with data management unit 10 via cables 24 and 26, respectively. Monitoring units 20 and 22 of FIG. 1 represent devices other than blood glucose monitor 16 that can be used to configure the invention for self-care health monitoring applications other than (or in addition to) diabetes care. For example, as is indicated in FIG. 1 the monitoring device 20 can be a peak-flow meter that provides a digital signal representative of the airflow that results when a person suffering from asthma or another chronic respiratory affliction expels a breath of air through the meter. As is indicated by monitor 22 of FIG. 1 various other devices can be provided for monitoring conditions such as blood pressure, pulse, and body temperature to thereby realize systems for self-care monitoring and control of conditions such as hypertension, certain heart conditions and various other afflictions and physical conditions. Upon understanding the hereinafter discussed aspects and features of the invention it will be recognized that the invention is easily implemented for these and other types of healthcare monitoring. In particular, monitors used in the practice of the invention can be arranged in a variety of ways as long as the data to be recorded or otherwise employed by handheld microprocessor unit and/or data management unit 10 is provided in serial format in synchronization with clock signals provided by data management unit 10. As is the case with blood glucose monitor 16, the additional monitors can be configured as plug-in units that are directly received by data management unit 10, or can be connected to data management unit 10 with cables (as shown in FIG. 1).

As is shown in FIG. 1, handheld microprocessor unit 12 includes a display screen 28 and a plurality of switches or keys (30, 32, 34, 36, and 38 in FIG. 1) which are mounted on a housing 40. Located in the interior of housing 40, but not shown in FIG. 1 are a microprocessor, memory circuits, and circuitry that interfaces switches 30, 32, 34, 36, and 38 with the microprocessor. Stored in the memory of program handheld microprocessor unit 12 is a set of program instructions that establishes a data protocol that allows handheld microprocessor unit 12 to perform digital data signal processing and generate desired data or graphics for display on display unit 28 when a program cartridge 42 is inserted in a slot or other receptacle in housing 40. That is, program cartridge 42 of FIG. 1 includes read-only memory units (or other memory means such as battery-powered random access memory) which store program instructions and data that adapt handheld microprocessor 12 for operation in a blood glucose monitoring system. More specifically, when the instructions and data of program cartridge 42 are combined with program instructions and data included in the internal memory circuits of handheld microprocessor unit 12 handheld microprocessor unit 12 is programmed for processing and displaying blood glucose information in the manner described below and additional monitors 22 to provide health monitoring for asthma and various other previously mentioned chronic conditions. In each case, the plurality of switches or keys (30, 32, 34, 36 and 38 in FIG. 1) are selectively operated to provide signals that result in pictorial and/or alphanumeric information being displayed by display unit 42.

Various devices are known that meet the above-set forth description of handheld microprocessor unit 12. For example, compact devices are available in which the plurality of keys allows alphanumeric entry and internal memory is provided for storing information such as names, addresses, phone numbers, and an appointment calendar. Small program cartridges or cards can be inserted in these devices to program the device for various purposes such as the playing of games, spreadsheet application, and foreign language translation sufficient for use in travel. More recently, less compact products that have more extensive computational capability and are generally called "palm top computers" have been introduced into the marketplace. These devices also can include provision for programming the device by means of an insertable program card or cartridge.

The currently preferred embodiments of the invention are configured and arranged to operate in conjunction with yet another type of handheld microprocessor unit. Specifically, in the currently preferred embodiments of the invention, program cartridge 42 is electrically and physically compatible with commercially available compact video game systems, such as the system manufactured by Nintendo of America Inc. under the trademark "GAME BOY." Configuring data management unit 10 and program cartridge 42 for operation with a handheld video game system has several advantages. For example, the display unit of such a device provides display resolution that allows the invention to display both multi-line alphanumeric information and graphical data. In this regard, the 160×144 pixel dot matrix-type liquid crystal display screen currently used in the above-referenced compact video game systems provides sufficient resolution for at least six lines of alphanumeric text, as well as allowing graphical representation of statistical data such as graphical representation of blood glucose test results for a day, a week, or longer.

Another advantage of realizing handheld microprocessor unit 12 in the form of a compact video game system is the relatively simple, yet versatile arrangement of switches that is provided by such a device. For example, as is indicated in FIG. 1 a compact video game system includes a control pad that allows an object displayed on display unit 42 to be moved in a selected direction (i.e., up-down or left-right). As also is indicated in FIG. 1, compact video game systems typically provide two pair of distinctly-shaped push button switches. In the arrangement shown in FIG. 1, a pair of spaced-apart circular push button switches (36 and 38) and a pair of elongate switches (32 and 34) are provided. The functions performed by the two pairs of switches is dependent upon the program instructions contained in each program cartridge 42.

Yet another advantage of utilizing a compact video game system for handheld microprocessor-based unit 12 of FIG. 1 is the widespread popularity and low cost of such units. In this regard, manufacture and sale of a data management unit blood glucose monitor 16 and program cartridge 42 that operate in conjunction with a compact microprocessor-based video allows the self-care health monitoring system of FIG. 1 to be manufactured and sold at a lower cost than could be realized in an arrangement in which handheld unit 12 is designed and manufactured solely for use in the system of FIG. 1.

An even further advantage of using a compact video game system for handheld microprocessor 12 is that such video game systems include means for easily establishing the electrical interconnection provided by cable 14 in FIG. 1. In particular, such compact video game systems include a connector mounted to the game unit housing (40 in FIG. 1) and a cable that can be connected between the connectors of two video game units to allow interactive operation of the two interconnected units (i.e., to allow contemporaneous game play by two players or competition between players as they individually play identical but separate games). In the preferred embodiments of the invention, the "two-player" cable supplied with the compact video game unit being used as handheld microprocessor unit 12 is used as cable 14 to establish serial data communication between the handheld microprocessor unit 12 (compact video game system) and data management unit 10. In these preferred embodiments, the program instructions stored on the memory of data management unit 10 and program cartridge 42 respectively program data management unit 10 and the compact video game system (i.e., handheld microprocessor unit 12) for interactive operation in which switches 30, 32, 34, 36 and 38 are used to control the operation of data management unit 10 (e.g., to select a particular operational mode such as performance of a blood glucose test or the display of statistical test data and, in addition, to control operation such as selection of an option during operation of the system in a particular operational mode). In each operational mode, data management unit 10 processes data in accordance with program instructions stored in the memory circuits of data management unit 10. Depending upon the operational mode selected by the user, data is supplied to data management unit 10 by blood glucose monitor 16 by additional monitors (20 and 22 in FIG. 1) or any interconnected computers or data processing facility (such as the hereinafter described user's computer 48 and clearinghouse 54 of FIG. 1) During such operation, mode switches 30, 32, 34, 36 and 38 are selectively activated so that signals are selectively coupled to the video game system (handheld microprocessor unit 12) and processed in accordance with program instructions stored in program cartridge 42. The signal processing performed by handheld microprocessor unit 12 results in the display of alphanumeric, symbolic, or graphic information on the video game display screen (i.e., display unit 28 in FIG. 1) which allow the user to control system operation and obtain desired test results and other information.

Although the above-discussed advantages apply to use of the invention by all age groups, employing a compact video game system in the practice of the invention is of special significance in monitoring a child's blood glucose or other health parameters. Children and young adults are familiar with compact video game systems. Thus, children will accept a health monitoring system incorporating a compact video game system more readily than a traditional system, even an embodiment of the invention that uses a different type of handheld microprocessor unit. Moreover, an embodiment of the invention that functions in conjunction with a compact video game system can be arranged to motivate children to monitor themselves more closely than they might otherwise by incorporating game-like features and/or animation in system instruction and test result displays. Similarly, the program instructions can be included in program cartridges 41, 42 and 43 (or additional cartridges) that allow children to select game-like displays that help educate the child about his or her condition and the need for monitoring.

With continued reference to FIG. 1, data management unit 10 of the currently preferred embodiments of the invention includes a data port 44 that allows communication between data management unit 10 and a personal computer 48 (or other programmable data processor). In the currently preferred embodiments of the invention, data port 44 is an RS-232 connection that allows serial data communication between data management unit 10 and personal computer 48. In the practice of the invention, personal computer 48 can be used to supplement data management unit 10 by, for example, performing more complex analyses of blood glucose and other data that has been supplied to and stored in the memory circuits of data management unit 10. With respect to embodiments of the invention configured for use by a child, personal computer 48 can be used by a parent or guardian to review and analyze the child's progress and to produce printed records for subsequent review by a healthcare professional. Alternatively, personal computer 48 can be used to supply data to data management unit 10 that is not conveniently supplied by using handheld microprocessor switches 30, 32, 34, 36 and 38 as an operator interface to the system shown in FIG. 1. For example, some embodiments of the invention may employ a substantial amount of alphanumeric information that must be entered by the system user. Although it is possible to enter such data by using switches 30, 32, 34, 36, and 38 in conjunction with menus and selection screens displayed on display screen 28 of FIG. 1 it may be more advantageous to use a device such as personal computer 48 for entry of such data. However, if personal computer 48 is used in this manner, some trade-off of system features may be required because data management unit 10 must be temporarily interconnected with personal computer 48 during these operations. That is, some loss of system mobility might result because a suitably programmed personal computer would be needed at each location at which data entry or analysis is to occur.

As is indicated in FIG. 1, data management unit 10 of the currently preferred embodiments of the invention also includes a modem that allows data communication between data management unit 10 and a remote computing facility identified in FIG. 1 as clearinghouse 54 via a conventional telephone line (indicated by reference numeral 50 in FIG. 1) and a modem 52 that interconnects clearinghouse 54 and telephone line 50. As shall be described in more detail, clearinghouse 54 computing facility 54 facilitates communication between a user of the system shown in FIG. 1 and his or her healthcare professional and can provide additional services such as updating system software. As is indicated by facsimile machine 55 of FIG. 1*a* primary function of clearinghouse 54 is providing the healthcare professional with standardized reports 56, which indicate both the current condition and condition trends of the system user. Although a single facsimile machine 55 is shown in FIG. 1, it will be recognized that numerous healthcare professionals (and hence facsimile machine 55) can be connected in signal communication with a clearinghouse 54.

Regardless of whether a compact video game system, another type of commercially available handheld microprocessor-based unit, or a specially designed unit is used, the preferred embodiments of FIG. 1 provide a self-care blood glucose monitoring system in which program cartridge (a) handheld microprocessor unit 12 for displaying instructions for performing the blood glucose test sequence and associated calibration and test procedures; (b) handheld microprocessor unit 12 for displaying (graphically or alphanumerically) statistical data such as blood glucose test results taken during a specific period of time (e.g., a day, week, etc.); (c) handheld microprocessor unit 12 for supplying control signals and signals representative of food intake or other useful information to data management unit 10; (d) handheld microprocessor unit 12 for simultaneous graphical display of blood glucose levels with information such as food intake; and, (e) handheld microprocessor unit 12 for displaying information or instructions from a healthcare professional that are coupled to data management unit 10 from a clearinghouse 54. The manner in which the arrangement of FIG. 1 implements the above-mentioned functions and others can be better understood with reference to FIGS. 2 and 3.

Figure 2:
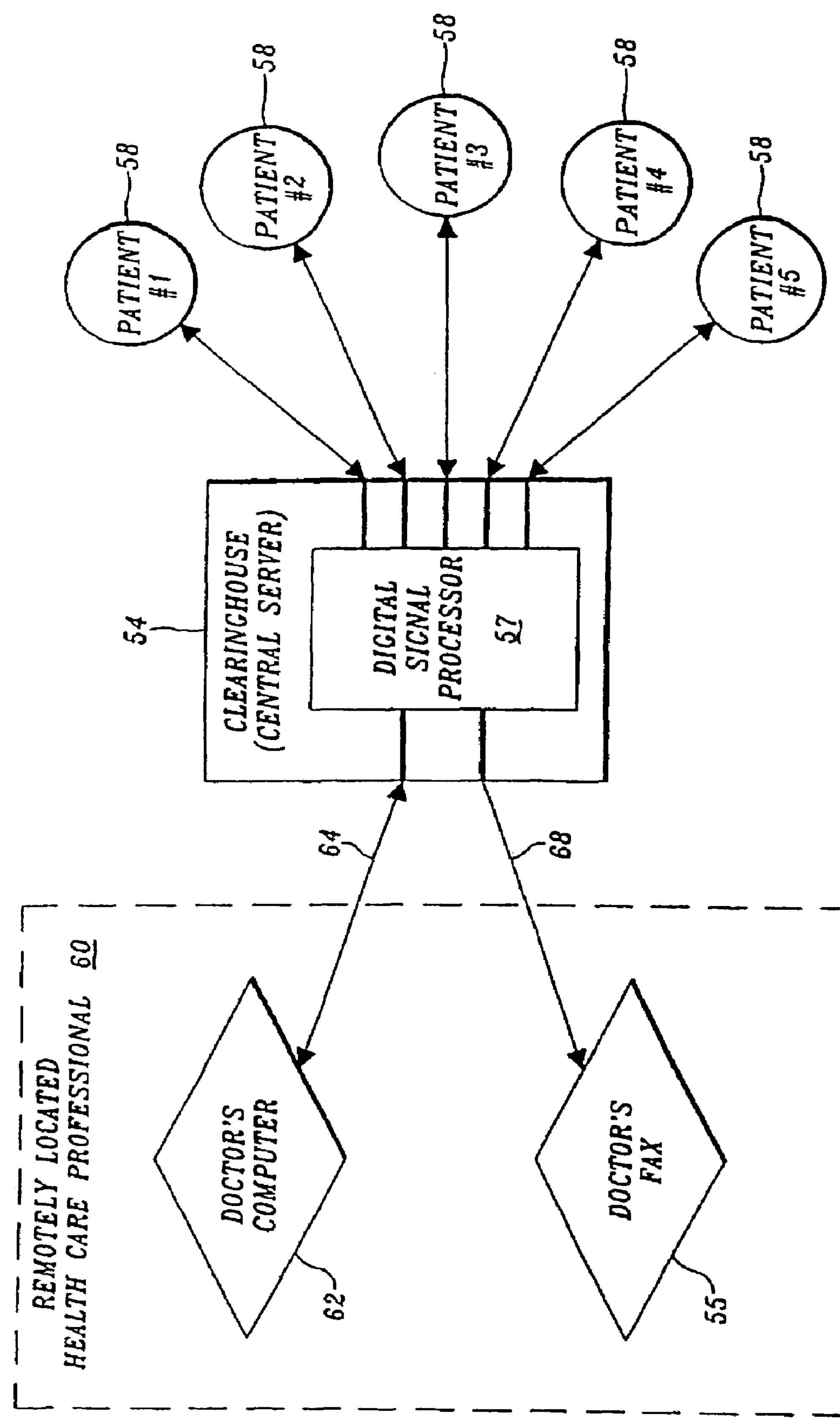
FIG. 2 diagrammatically illustrates monitoring systems constructed in accordance with the invention connected in signal communication with a remotely located computing facility which includes provision for making the data supplied by the monitoring system of the invention available to a designated healthcare professional and/or for providing data and instructions to the system user.

Referring first to FIG. 2, clearinghouse 54 receives data from a plurality of self-care microprocessor-based healthcare systems of the type shown in FIG. 1, with the individual self-care health monitoring systems being indicated in FIG. 2 by reference numeral 58. Preferably, the data supplied to clearinghouse 54 by each individual self-care health monitoring system 58 consists of "raw data," i.e., test results and related data that was stored in memory circuits of data management unit 10, without further processing by data management unit 10. For example, with respect to the arrangement shown in FIG. 1, blood glucose test results and associated data such as food intake information, medication dosage and other such conditions are transmitted to clearinghouse 54 and stored with a digitally encoded signal that identifies both the source of the information (i.e., the system user or patient) and those having access to the stored information (i.e., the system user's doctor or other healthcare professional).

As shall be recognized upon understanding the manner in which it operates, clearinghouse 54 can be considered to be a central server for the various system users (58 in FIG. 2) and each healthcare professional 60. In that regard, clearinghouse 54 includes conventionally arranged and interconnected digital processing equipment (represented in FIG. 2 by digital signal processor 57) which receives digitally encoded information from a user 58 or healthcare professional processes the information as required; stores the information (processed or unprocessed) in memory if necessary; and, transmits the information to an intended recipient (i.e., user 58 or healthcare professional 60).

In FIG. 2 rectangular outline 60 represents one of numerous remotely located healthcare professionals who can utilize clearinghouse 54 and the arrangement described relative to FIG. 1 in monitoring and controlling patient healthcare programs. Shown within outline 60 is a computer 62 (e.g., personal computer), which is coupled to clearinghouse 54 by means of a modem (not shown in FIG. 2) and a telephone line 64. Also shown in FIG. 2 is the previously mentioned facsimile machine 55, which is coupled to clearinghouse 54 by means of a second telephone line 68. Using the interface unit of computer 62 (e.g., a keyboard or pointing device such as a mouse), the healthcare professional can establish data communication between computer 62 and clearinghouse 54 via telephone line 64. Once data communication is established between computer 62 and clearinghouse 54 patient information can be obtained from clearinghouse 54 in a manner similar to the manner in which subscribers to various database services access and obtain information. In particular, the healthcare professional can transmit an authorization code to clearinghouse 54 that identifies the healthcare professional as an authorized user of the clearinghouse and, in addition, can transmit a signal representing the patient for which healthcare information is being sought. As is the case with conventional database services and other arrangements, the identifying data is keyed into computer 62 by means of a conventional keyboard (not shown in FIG. 2) in response to prompts that are generated at clearinghouse 54 for display by the display unit of computer 62 (not shown in FIG. 2).

Depending upon the hardware and software arrangement of clearinghouse 54 and selections made by the healthcare professional via computer 62 patient information can be provided to the healthcare professional in different ways. For example, computer 62 can be operated to access data in the form that it is stored in the memory circuits of clearinghouse 54 (i.e., raw data that has not been processed or altered by the computational or data processing arrangements of clearinghouse 54). Such data can be processed, analyzed, printed and/or displayed by computer 62 using commercially available or custom software. On the other hand, various types of analyses may be performed by clearinghouse 54 with the results of the analyses being transmitted to the remotely located healthcare professional 60. For example, clearinghouse 54 can process and analyze data in a manner identical to the processing and analysis provided by the self-care monitoring system of FIG. 1. With respect to such processing and any other analysis and processing provided by clearinghouse 54 results expressed in alphanumeric format can be sent to computer 62 via telephone line 64 and the modem associated with computer 62 with conventional techniques being used for displaying and/or printing the alphanumeric material for subsequent reference.

The arrangement of FIG. 2 also allows the healthcare professional to send messages and/or instructions to each patient via computer 62 telephone line 64 and clearinghouse 54. In particular, clearinghouse 54 can be programmed to generate a menu that is displayed by computer 62 and allows the healthcare professional to select a mode of operation in which information is to be sent to clearinghouse 54 for subsequent transmission to a user of the system described relative to FIG. 1. This same menu (or related submenus) can be used by the healthcare professional to select one or more modes of operation of the above-described type in which either unmodified patient data or the results of data that has been analyzed by clearinghouse 54 is provided to the healthcare provider via computer 62 and/or facsimile machine 55.

In the currently contemplated arrangements, operation of the arrangement of FIG. 2 to provide the user of the invention with messages or instructions such as changes in medication or other aspects of the healthcare program is similar to the operation that allows the healthcare professional to access data sent by a patient, i.e., transmitted to clearinghouse 54 by a data management unit 10 of FIG. 1. The process differs in that the healthcare professional enters the desired message or instruction via the keyboard or other interface unit of computer 62. Once the data is entered and transmitted to clearinghouse 54 it is stored for subsequent transmission to the user for whom the information or instruction is intended.

With respect to transmitting stored messages or instructions to a user of the invention, at least two techniques are available. The first technique is based upon the manner in which operational modes are selected in the practice of the invention. Specifically, in the currently preferred embodiments of the invention, program instructions that are stored in data management unit 10 and program cartridge 42 cause the system of FIG. 1 to generate menu screens which are displayed by display unit 28 of handheld microprocessor unit 12. The menu screens allow the system user to select the basic mode in which the system of FIG. 1 is to operate and, in addition, allow the user to select operational subcategories within the selected mode of operation. Various techniques are known to those skilled in the art for displaying and selecting menu items. For example, in the practice of this invention, one or more main menus can be generated and displayed which allow the system user to select operational modes that may include: (a) a monitor mode (e.g., monitoring of blood glucose level); (b) a display mode (e.g., displaying previously obtained blood glucose test results or other relevant information); (c) an input mode (e.g., a mode for entering data such as providing information that relates to the healthcare regimen, medication dosage, food intake, etc.); and, (d) a communications mode (for establishing a communication link between data management unit 10 and personal computer 48 of FIG. 1 or between data management unit 10 and a remote computing facility such as clearinghouse 54 of FIG. 2.

In embodiments of the invention that employ a compact video game system for handheld microprocessor unit 12 the selection of menu screens and the selection of menu screen items preferably is accomplished in substantially the same manner as menu screens and menu items are selected during the playing of a video game. For example, the program instructions stored in data management unit 10 and program cartridge 42 of the arrangement of FIG. 1 can be established so that a predetermined one of the compact video game switches (e.g., switch 32 in FIG. 1) allows the system user to select a desired main menu in the event that multiple main menus are employed. When the desired main menu is displayed, operation by the user of control pad 30 allows a cursor or other indicator that is displayed on the menu to be positioned adjacent to or over the menu item to be selected. Activation of a switch (e.g., switch 36 of the depicted handheld microprocessor unit causes the handheld microprocessor unit 12) and/or data management unit 10 to initiate the selected operational mode or, if selection of operational submodes is required, causes handheld microprocessor unit 12 to display a submenu.

In view of the above-described manner in which menus and submenus are selected and displayed, it can be recognized that the arrangement of FIG. 1 can be configured and arranged to display a menu or submenu item that allows the user to obtain and display messages or instructions that have been provided by a healthcare professional and stored in clearinghouse 54. For example, a submenu that is generated upon selection of the previously mentioned communications mode can include submenu items that allow the user to select various communication modes, including a mode in which serial data communication is established between data management unit 10 and clearinghouse 54 and data management unit 10 transmits a message status request to clearinghouse 54. When this technique is used, the data processing system of clearinghouse 54 is programmed to search the clearinghouse memory to determine whether a message exists for the user making the request. Any messages stored in memory for that user are then transmitted to the user and processed for display on display unit 28 of handheld microprocessor unit 12. If no messages exist, clearinghouse 54 transmits a signal that causes display unit 28 to indicate "no messages." In this arrangement, clearinghouse 54 preferably is programmed to store a signal indicating that a stored message has been transmitted to the intended recipient (user). Storing such a signal allows the healthcare professional to determine that messages sent to clearinghouse 54 for forwarding to a patient have been transmitted to that patient. In addition, the program instructions stored in data management unit 10 of FIG. 1 preferably allow the system user to designate whether received messages and instructions are to be stored in the memory of data management unit 10 for subsequent retrieval or review. In addition, in some instances it may be desirable to program clearinghouse 54 and data management unit 10 so that the healthcare professional can designate (i.e., flag) information such as changes in medication that will be prominently displayed to the user (e.g., accompanied by a blinking indicator) and stored in the memory of data management unit 10 regardless of whether the system user designates the information for storage.

A second technique that can be used for forwarding messages or instructions to a user does not require the system user to select a menu item requesting transmission by clearinghouse 54 of messages that have been stored for forwarding to that user. In particular, clearinghouse 54 can be programmed to operate in a manner that either automatically transmits stored messages for that user when the user operates the system of FIG. 1 to send information to the clearinghouse or programmed to operate in a manner that informs the user that messages are available and allows the user to access the messages when he or she chooses to do so.

Practicing the invention in an environment in which the healthcare professional uses a personal computer in some or all of the above-discussed ways can be very advantageous. On the other hand, the invention also provides healthcare professionals timely information about system users without the need for a computer (62 in FIG. 2) or any equipment other than a conventional facsimile machine (55 in FIGS. 1 and 2) Specifically, information provided to clearinghouse 54 by a system user 58 can be sent to a healthcare professional 60 via telephone line 68 and facsimile machine 55 with the information being formatted as a standardized graphic or textual report (56 in FIG. 1) Formatting a standardized report 56 (i.e., analyzing and processing data supplied by blood glucose monitor 16 or other system monitor or sensor) can be effected either by data management unit 10 or within the clearinghouse facility 54. Moreover, various standardized reports can be provided (e.g., the textual and graphic displays discussed below relating to FIGS. 6-10) Preferably, the signal processing arrangement included in clearinghouse 54 allows each healthcare professional 60 to select which of several standardized reports will be routinely transmitted to the healthcare professionals' facsimile machine 55 and, to do so on a patient-by-patient (user-by-user) basis.

Figure 3:
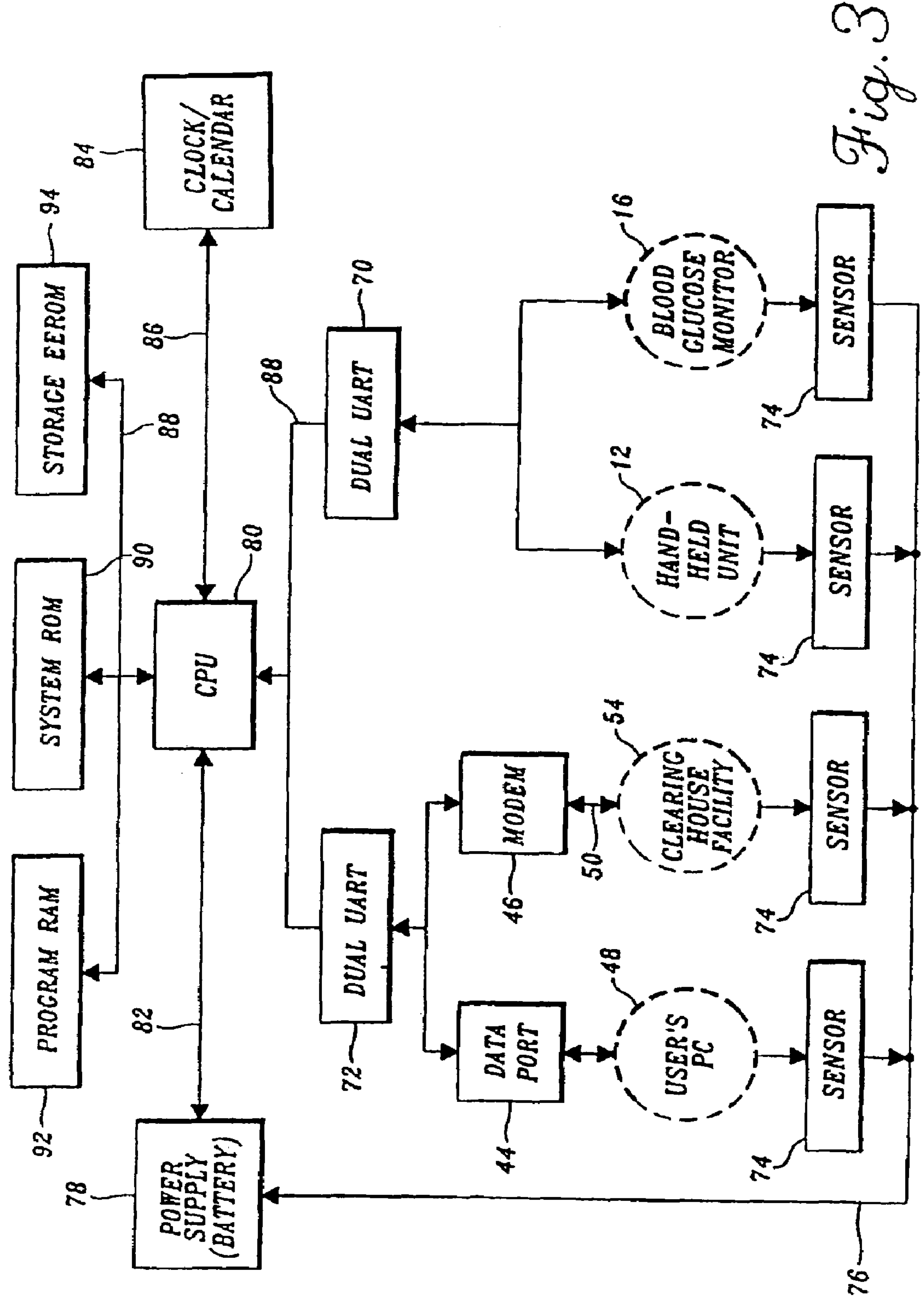
FIG. 3 is a block diagram diagrammatically depicting the structural arrangement of the system data management unit and its interconnection with other components of the system shown in FIG. 1.

FIG. 3 illustrates the manner in which data management unit 10 is arranged and interconnected with other system components for effecting the above-described operational aspects of the invention and additional aspects that are described relative to FIGS. 4-10. As is symbolically indicated in FIG. 3, handheld microprocessor unit 12 and blood glucose monitor 16 are connected to a dual universal asynchronous receiver transmitter 70 (e.g., by cables 14 and 18 of FIG. 1, respectively). As also is indicated in FIG. 3 when a system user connects a personal computer 48 (or other programmable digital signal processor) to data port 44 signal communication is established between personal computer 48 and a second dual universal asynchronous receiver transmitter 72 of data management unit 10. Additionally, dual universal asynchronous receiver transmitter 72 is coupled to modem 46 so that data communication can be established between data management unit 10 and a remote clearinghouse 54 of FIGS. 1 and 2.

Currently preferred embodiments of data management unit 10 include a plurality of signal sensors 74, with an individual signal sensor being associated with each device that is (or may be) interconnected with data management unit 10. As previously discussed and as is indicated in FIG. 3, these devices include handheld microprocessor unit 12, blood glucose monitor 16, personal computer 48, remote computing facility 54, and, in addition, peak-flow meter 20 or other additional monitoring devices 22. Each signal sensor 74 that is included in data management unit 10 is electrically connected for receiving a signal that will be present when the device with which that particular signal sensor is associated is connected to data management unit 10 and, in addition, is energized (e.g., turned on). For example, in previously mentioned embodiments of the invention in which data port 44 is an RS-232 connection, the signal sensor 74 that is associated with personal computer 48 can be connected to an RS-232 terminal that is supplied power when a personal computer is connected to data port 44 and the personal computer is turned on. In a similar manner, the signal sensor 74 that is associated with clearinghouse 54 can be connected to modem 46 so that the signal sensor 74 receives an electrical signal when modem 46 is interconnected to a remote computing facility (e.g., clearinghouse 54 of FIG. 2) via a telephone line 50.

In the arrangement of FIG. 3, each signal sensor 74 is a low power switch circuit (e.g., a metal-oxide semiconductor field-effect transistor circuit), which automatically energizes data management unit 10 whenever any one (or more) of the devices associated with signal sensors 74 is connected to data management unit 10 and is energized. Thus, as is indicated in FIG. 3 by signal path 76 ach signal sensor is 74 interconnected with power supply 78 which supplies operating current to the circuitry of data management unit 10 and typically consists of one or more small batteries (e.g., three AAA alkaline cells). The microprocessor and other conventional circuitry that enables data management unit 10 to process system signals in accordance with stored program instructions is indicated in FIG. 3 by central processing unit (CPU) 80. As is indicated in FIG. 3 by interconnection 82 between CPU 80 and battery 78. CPU 80 receives operating current from power supply 78 with power being provided only when one or more of the signal sensors 74 are activated in the previously described manner. A clock/calendar circuit 84 is connected to CPU (80 via signal path 86 in FIG. 3) to allow time and date tagging of blood glucose tests and other information. Although not specifically shown in FIG. 3, operating power is supplied to clock/calendar 84 at all times.

In operation, CPU 80 receives and sends signals via a data bus (indicated by signal path 88 in FIG. 3) which interconnects CPU 80 with dual universal asynchronous receiver transmitters 70 and 72. The data bus 88 also interconnects CPU 80 with memory circuits which, in the depicted embodiment, include a system read-only memory (ROM) 90 a program random access memory (RAM) 92 and an electronically erasable read-only memory (EEROM) 94. System ROM 90 stores program instructions and any data required in order to program data management unit 10 so that data management unit 10 and a handheld microprocessor unit 12 that is programmed with a suitable program cartridge 42 provide the previously discussed system operation and, in addition, system operation of the type described relative to FIGS. 4-10. During operation of the system, program RAM 92 provides memory space that allows CPU 80 to carry out various operations that are required for sequencing and controlling the operation of the system of FIG. 1. In addition, RAM 92 can provide memory space that allows external programs (e.g., programs provided by clearinghouse 54 to be stored and executed. EEROM 94 allows blood glucose test results and other data information to be stored and preserved until the information is no longer needed (i.e., until purposely erased by operating the system to provide an appropriate erase signal to EEROM 94).

Figures 4, 5, 6, 7:
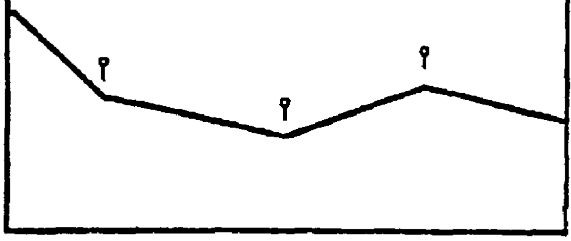
FIGS. 4-10 depict typical system screen displays of data and information that can be provided by the arrangements shown in FIGS. 1-3.

FIGS. 4-10 illustrate typical screen displays that are generated by the arrangement of the invention described relative to FIGS. 1-3. Reference will first be made to FIGS. 4 and 5 which exemplify screen displays that are associated with operation of the invention in the blood glucose monitoring mode. Specifically, in the currently preferred embodiments of the invention, blood glucose monitor 16 operates in conjunction with data management unit 10 and handheld microprocessor unit 12 to: (a) a test or calibration sequence in which tests are performed to confirm that the system is operating properly; and, (b) the blood glucose test sequence in which blood glucose meter 16 senses the user's blood glucose level. Suitable calibration procedures for blood glucose monitors are known in the art. For example, blood glucose monitors often are supplied with a "code strip," that is inserted in the monitor and results in a predetermined value being displayed and stored in memory at the conclusion of the code strip calibration procedure. When such a code strip calibration procedure is used in the practice of the invention, the procedure is selected from one of the system menus. For example, if the system main menu includes a "monitor" menu item, a submenu displaying system calibration options and an option for initiating the blood glucose test may be displayed when the monitor menu item is selected. When a code strip option is available and selected, a sequence of instructions is generated and displayed by display screen 28 of handheld microprocessor unit 12 to prompt the user to insert the code strip and perform all other required operations. At the conclusion of the code strip calibration sequence, display unit 28 of handheld microprocessor unit 12 displays a message indicating whether or not the calibration procedure has been successfully completed. For example, FIG. 4 illustrates a screen display that informs the system user that the calibration procedure was not successful and that the code strip should be inserted again (i.e., the calibration procedure is to be repeated). As is indicated in FIG. 4, display screens that indicate a potential malfunction of the system include a prominent message such as the "Attention" notation included in the screen display of FIG. 4.

As previously indicated, the blood glucose test sequence that is employed in the currently preferred embodiment of the invention is of the type in which a test strip is inserted in a receptacle that is formed in the blood glucose monitor. A drop of the user's blood is then applied to the test strip and a blood glucose sensing sequence is initiated. When the blood glucose sensing sequence is complete, the user's blood glucose level is displayed.

In the practice of the invention, program instructions stored in data management unit 10 (e.g., system ROM 90 of FIG. 3) and program instructions stored in program cartridge 42 of handheld microprocessor unit 12 cause the system to display step-by-step monitoring instructions to the system user and, in addition, preferably result in display of diagnostic messages if the test sequence does not proceed in a normal fashion. Although currently available self-contained microprocessor-based blood glucose monitors also display test instruction and diagnostic messages, the invention provides greater message capacity and allows multi-line instructions and diagnostic messages that are displayed in easily understood language rather than cryptic error codes and abbreviated phraseology that is displayed one line or less at a time. For example, as is shown in FIG. 5 the complete results of a blood glucose test (date, time of day, and blood glucose level in milligrams per deciliter) can be concurrently displayed by display screen 28 of handheld microprocessor unit 12 along with an instruction to remove the test strip from blood glucose monitor 16. As previously mentioned, when the blood glucose test is complete, the time and date tagged blood glucose test result is stored in the memory circuits of data management unit 10 (e.g., stored in EEPROM 94 of FIG. 3)

The arrangement shown and described relative to FIGS. 1-3 also is advantageous in that data relating to food intake, concurrent medication dosage and other conditions easily can be entered into the system and stored with the time and date tagged blood glucose test result for later review and analysis by the user and/or his or her healthcare professional. Specifically, a menu generated by the system at the beginning or end of the blood glucose monitoring sequence can include items such as "hypoglycemic" and "hyperglycemic," which can be selected using the switches of handheld microprocessor unit 12 (e.g., operation of control pad 30 and switch 36 in FIG. 1) to indicate the user was experiencing hypoglycemic or hyperglycemic symptoms at the time of monitoring blood glucose level. Food intake can be quantitatively entered in terms of "Bread Exchange" units or other suitable terms by, for example, selecting a food intake menu item and using a submenu display and the switches of handheld microprocessors 2 to select and enter the appropriate information. A similar menu item—submenu selection process also can be used to enter medication data such as the type of insulin used at the time of the glucose monitoring sequence and the dosage.

As was previously mentioned, program instructions stored in data management unit 10 and program instructions stored in program cartridge 42 of handheld microprocessor unit 12 enable the system to display statistical and trend information either in a graphic or alphanumeric format. As is the case relative to controlling other operational aspects of the system, menu screens are provided that allow the system user to select the information that is to be displayed. For example, in the previously discussed embodiments in which a system menu includes a "display" menu item, selection of the menu item results in the display of one or more submenus that list available display options. For example, in the currently preferred embodiments, the user can select graphic display of blood glucose test results over a specific period of time, such as one day, or a particular week. Such selection results in displays of the type shown in FIGS. 6 and 7 respectively. When blood glucose test results for a single day are displayed (FIG. 6) the day of the week and date can be displayed along with a graphic representation of changes in blood glucose level between the times at which test results were obtained. In the display of FIG. 6, small icons identify points on the graphic representation that correspond to the blood glucose test results (actual samples). Although not shown in FIG. 6, coordinate values for blood glucose level and time of day can be displayed if desired. When the user chooses to display a weekly trend graph (FIG. 7) the display generated by the system is similar to the display of a daily graph, having the time period displayed in conjunction with a graph that consists of lines interconnecting points that correspond to the blood glucose test results.

Figures 8, 9, 10:
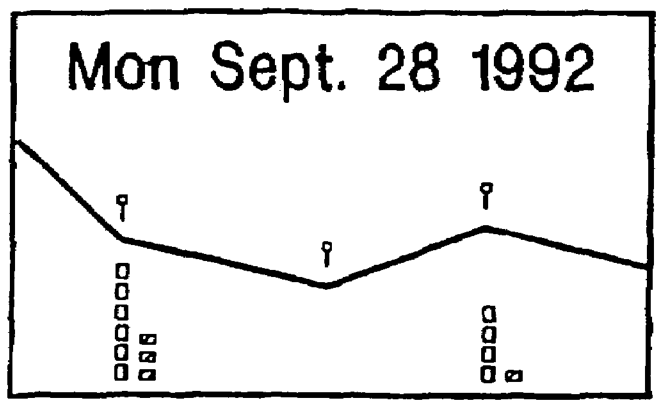

The screen display shown in FIG. 8 is representative of statistical data that can be determined by the system of FIG. 1 (using conventional computation techniques) and displayed in alphanumeric format. As previously mentioned, such statistical data and information in various other textual and graphic formats can be provided to a healthcare professional (60 in FIG. 2) in the form of a standardized report 56 (FIG. 1) that is sent by clearinghouse 54 to facsimile machine 55. In the exemplary screen display of FIG. 8, statistical data for blood glucose levels over a period of time (e.g., one week) or, alternatively, for a specified number of monitoring tests is provided. In the exemplary display of FIG. 8 the system (data management unit 10 or clearinghouse 54) also calculates and displays (or prints) the average blood glucose level and the standard deviation. Displayed also is the number of blood glucose test results that were analyzed to obtain the average and the standard deviation; the number of test results under a predetermined level (50 milligrams per deciliter in FIG. 8) and the number of blood glucose tests that were conducted while the user was experiencing hypoglycemic symptoms. As previously noted, in the preferred embodiments of the invention, a screen display that is generated during the blood glucose monitoring sequence allows the user to identify the blood sample being tested as one taken while experiencing hyperglycemic or hypoglycemic symptoms and, in addition, allows the user to specify other relevant information such as food intake and medication information.

The currently preferred embodiments of the invention also allow the user to select a display menu item that enables the user to sequentially address, in chronological order, the record of each blood glucose test. As is indicated in FIG. 9, each record presented to the system user includes the date and time at which the test was conducted, the blood glucose level, and any other information that the user provided. For example, the screen display of FIG. 9 indicates that the user employed handheld microprocessor unit 12 as an interface to enter data indicating use of 12.5 units of regular insulin; 13.2 units of "NPH" insulin; food intake of one bread exchange unit; and pre-meal hypoglycemic symptoms.

Use of data management unit 10 in conjunction with handheld microprocessor unit 12 also allows display (or subsequent generation of a standardized report showing blood glucose test results along with food intake and/or medication information. For example, shown in FIG. 10 is a daily graph in which blood glucose level is displayed in the manner described relative to FIG. 6. Related food intake and medication dosage is indicated directly below contemporaneous blood glucose levels by vertical bar graphs.

It will be recognized by those skilled in the art that the above-described screen displays and system operation can readily be attained with conventional programming techniques of the type typically used in programming microprocessor arrangements. It also will be recognized by those skilled in the art that various other types of screen displays can be generated and, in addition, that numerous other changes can be made in the embodiments described herein without departing from the scope and the spirit of the invention.

Figure 11:
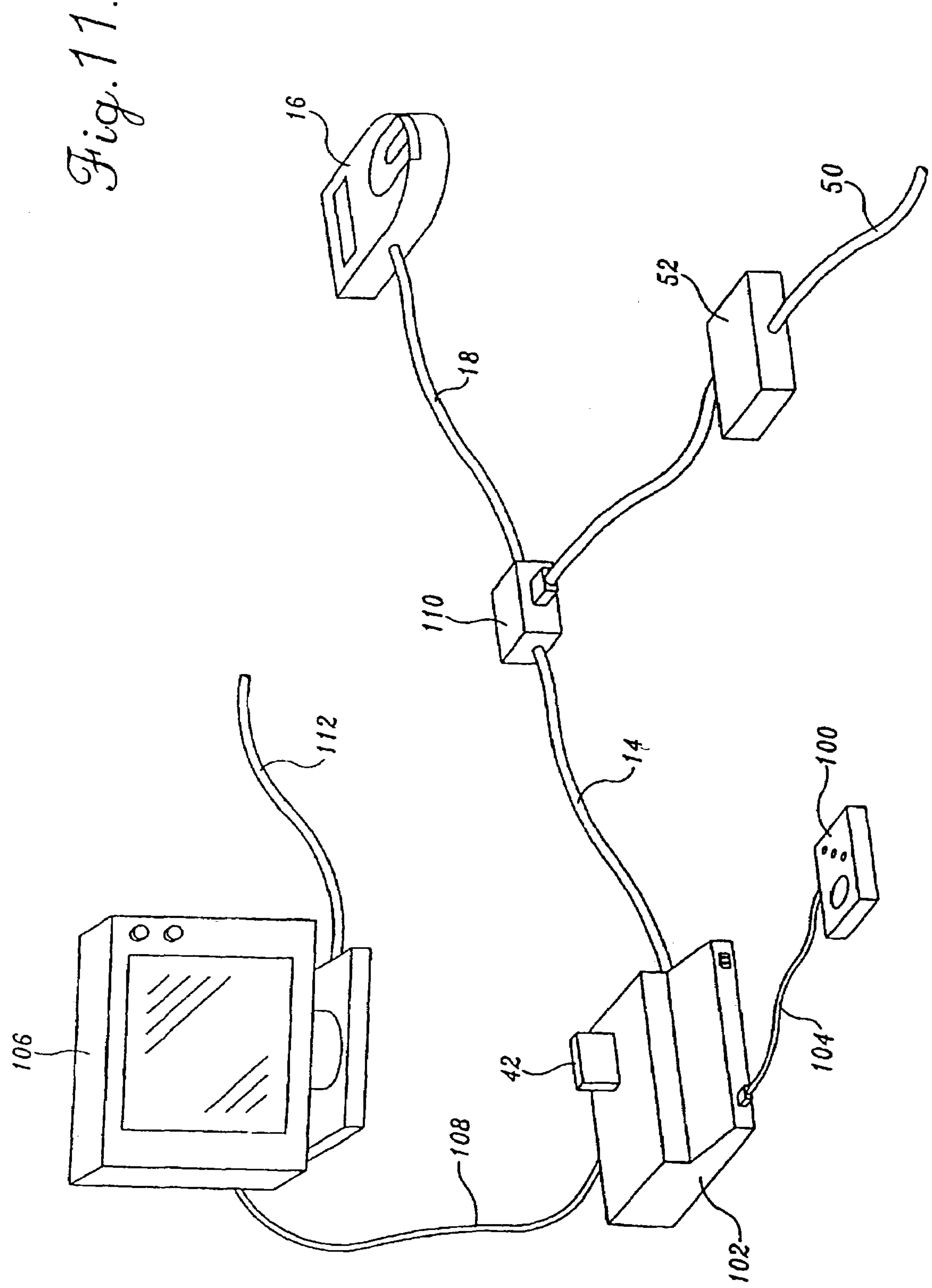
FIG. 11 diagrammatically illustrates an alternative healthcare monitoring system that is arranged in accordance with the invention.

It will also be recognized by those skilled in the art that the invention can be embodied in forms other than the embodiments described relative to FIGS. 1-10. For example, the invention can employ compact video game systems that are configured differently than the previously discussed handheld video game systems and palm-top computers. More specifically, as is shown in FIG. 11 a self-care health monitoring system arranged in accordance with the invention can employ a compact video game system of the type that includes one or more controllers 100 that are interconnected to a game console 102 via cable 104. As is indicated in FIG. 11, game console 102 is connected to a video monitor or television 106 by means of a cable 108. Although differing in physical configuration, controller 100, game console 102 and the television or video monitor 106 collectively function in the same manner as the handheld microprocessor 12 of FIG. 1. In that regard, a program cartridge 42 is inserted into a receptacle contained in game console 102 with program cartridge 42 including stored program instructions for controlling microprocessor circuitry that is located inside game console 102. Controller 100 includes a control pad or other device functionally equivalent to control pad 30 of FIG. 1 and switches that functionally correspond to switches 32-38 of FIG. 1.

Regardless of whether the invention is embodied with a handheld microprocessor unit (FIG. 1) or an arrangement such as the compact video game system (FIG. 11) in some cases it is both possible and advantageous to apportion the signal processing functions and operations differently than was described relative to FIGS. 1-10. For example, in some situations, the microprocessor-based unit that is programmed by a card or cartridge (e.g., handheld unit 12 of FIG. 1 or compact video game console 102 of FIG. 1) includes memory and signal processing capability that allows the microprocessor to perform all or most of the functions and operations attributed to data management unit 10 of the embodiments discussed relative to FIGS. 1-10. That is, the digitally encoded signal supplied by blood glucose monitor 16 (or one of the other monitors 20 and 22 of FIG. 1) can be directly coupled to the microprocessor included in game console 102 of FIG. 11 or handheld microprocessor 12 of FIG. 1. In such an arrangement, the data management unit is a relatively simple signal interface (e.g., interface unit 110 of FIG. 11) the primary purpose of which is carrying signals between the blood glucose monitor 16 (or other monitor) and the microprocessor of game console 102 (FIG. 11) or handheld unit (FIG. 1). In some situations, the interface unit may consist primarily or entirely of a conventional cable arrangement such as a cable for interconnection between RS232 data ports or other conventional connection arrangements. On the other hand, as is shown in FIG. 11, signal interface 110 can either internally include or be connected to a modem 52, which receives and transmits signals via a telephone line 50 in the manner described relative to FIGS. 1 and 2.

It also should be noted that all or a portion of the functions and operations attributed to data management unit 10 of FIG. 1 can be performed by microprocessor circuitry located in blood glucose monitor 16 (or other monitor that is used with the system). For example, a number of commercially available blood glucose monitors include a clock/calendar circuit of the type described relative to FIG. 3 and, in addition, include microprocessor circuitry for generating visual display signals and signals representative of both current and past values of monitored blood glucose level. Conventional programming and design techniques can be employed to adapt such commercially available units for the performance of the various functions and operations attributed in the above discussion of FIGS. 1-11 to data management unit 10 and/or the microprocessors of handheld unit and compact video console 102. In arrangements in which the blood glucose monitor (or other system monitor) includes a microprocessor that is programmed to provide signal processing in the above-described manner, the invention can use a signal interface unit 110 of the above type. That is, depending upon the amount of signal processing effected by the monitoring unit (e.g., blood glucose monitor 16) and the amount of signal processing performed by the microprocessor of video game console 102 (or handheld unit the signal interface required ranges from a conventional cable (e.g., interconnection of RS232 ports) to an arrangement in which signal interface 110 is arranged for signal communication with an internal or external modem (e.g., modem 52 of FIG. 11) or an arrangement in which signal interface provides only a portion of the signal processing described relative to FIGS. 1-10.

The invention also is capable of transmitting information to a remote location (e.g., clearinghouse 54 and/or a remotely located healthcare professional) by means other than conventional telephone lines. For example, a modem (52 in FIGS. 1 and 11) that is configured for use with a cellular telephone system can be employed to transmit the signals provided by the healthcare monitoring system to a remote location via modulated RF transmission. Moreover, the invention can be employed with various digital networks such as recently developed interactive voice, video and data systems such as television systems in which a television and user interface apparatus is interactively coupled to a remote location via coaxial or fiber optic cable and other transmission media (indicated in FIG. 11 by cable 112 which is connected to television or video monitor 106). In such an arrangement, compact video game controller 100 and the microprocessor of video game console 102 can be programmed to provide the user interface functions required for transmission and reception of signals via the interactive system. Alternatively, the signals provided by video game console 102 (or handheld unit 12 if FIG. 1) can be supplied to the user interface of the interactive system (not shown in FIG. 11) in a format that is compatible with the interactive system and allows the system user interface to be used to control signal transmission between the healthcare system and a remote facility such as clearinghouse 54, FIGS. 1 and 2.

The invention claimed is:

1. A physiological data monitoring system comprising:

(a) at least one central server arranged to receive and communicate data;

(b) at least one microprocessor-based subsystem (i) including at least one microprocessor, a display and a memory, (ii) configured to present information on the display and provide a digital signal representative of physiological data from a person, and (iii) arranged to establish a communication link to the central server, facilitate a communication of the physiological data on the communication link to the central server and disconnect the communication link after the communication of the physiological data has finished; and (c) at least one health care professional computer in signal communication with the central server to receive health-related information based on the physiological data received from the microprocessor-based subsystem, wherein the central server stores additional data received from the health care professional computer and provides the additional data to the microprocessor-based subsystem to run after the communication link has been established by the microprocessor-based subsystem, the additional data including instructions to the person effecting a change in a treatment regimen based on earlier physiological data.

2. The system of claim 1, wherein the microprocessor-based subsystem further includes (a) a data management unit adapted for digital data signal processing; and (b) a monitoring device that can transmit data to be received directly by the data management unit or that can be connected to data management unit.

3. The system of claim 2, wherein at least one monitoring device is (a) configured to monitor at least one person's condition; and (b) connected to facilitate communication of data related to the monitored condition to the central server.

4. The system of claim 3, wherein at least one monitoring device includes one or more of the set consisting of (a) a blood glucose monitor;

(b) a blood pressure monitor;

(c) a pulse monitor; and (d) a body temperature monitor.

5. The system of claim 1, wherein the at least one microprocessor, the display and the memory is in a handheld device.

6. The system of claim 1, wherein the microprocessor-based subsystem displays pictorial information.

7. The system of claim 1, wherein the microprocessor-based subsystem displays animated information.

8. The system of claim 1, the microprocessor-based subsystem further includes at least one of an insertable program card or cartridge.

9. The system of claim 8, wherein instructions in the program card or cartridge are configured to facilitate the monitoring.

10. The system of claim 1, further including at least one personal computer connected for use by the person.

11. The system of claim 1, wherein the system is configured to use the physiological data to process a report.

12. The system of claim 11, wherein the report includes graphs and/or icons.

13. The system of claim 11, wherein the report includes information for a period of time.

14. The system of claim 1, wherein the information includes at least one message.

15. The system of claim 14, wherein the message is transmitted to a specific person.

16. The system of claim 1, wherein the information includes step-by-step instructions.

17. The system of claim 1, wherein the information is educational or motivational.

18. The system of claim 1, wherein the presentation of information can be controlled using at least one menu.

19. The system of claim 1, wherein the system is configured to enable the additional data to be provided for storage in the memory.

20. The system of claim 19, further comprising at least one of an insertable program card or cartridge and wherein at least part of the additional data is stored on the card or on a cartridge.

21. A physiological data monitoring system comprising:

(a) at least one central server arranged to receive and communicate data;

(b) at least one microprocessor-based subsystem (i) including at least one microprocessor, a display and a memory, (ii) configured to present information on the display and provide a digital signal representative of physiological data from a person, and (iii) arranged to establish a communication link to the central server, facilitate a communication of the physiological data on the communication link to the central server and disconnect the communication link after the communication of the physiological data has finished; and (c) at least one health care professional computer in signal communication with the central server to receive health-related information based on the physiological data received from the microprocessor-based subsystem, wherein the central server is configured to send data to the microprocessor-based subsystem in response to receiving a request from the microprocessor-based subsystem after the communication link has been established by the microprocessor-based subsystem, where the central server stores additional data received from the health care professional computer and provides the additional data to the microprocessor-based subsystem after the communication link has been established by the microprocessor-based subsystem.

22. A physiological data monitoring system comprising:

(a) at least one central server arranged to receive and communicate data;

(b) at least one microprocessor-based subsystem (i) including at least one microprocessor, a display and a memory, (ii) configured to present information on the display and provide a digital signal representative of physiological data from a person, and (iii) arranged to establish a communication link to the central server, facilitate a communication of the physiological data on the communication link to the central server and disconnect the communication link after the communication of the physiological data has finished, wherein the central server is configured to (i) wait for the microprocessor-based system to turn on and establish the communication link (ii) automatically send one or more messages viewable by the person to the microprocessor-based system before the communication link is disconnected, and (iii) notify the person of the messages; and (c) at least one health care professional apparatus adapted to receive communication from the central server to receive health-related information based on the physiological data received from the microprocessor-based subsystem and to send data to the central server;

where the central server stores additional data received from the health care professional computer and provides the additional data to the microprocessor-based subsystem after the communication link has been established by the microprocessor-based subsystem.

23. The apparatus according to claim 22, wherein the health care professional apparatus is configured to automatically receive fax reports about health related information.

24. The apparatus according to claim 22, wherein the health care professional apparatus selects from standardized reports related to the health related information.

25. A user-related data monitoring system comprising:

(a) at least one central server arranged to receive and communicate data;

(b) at least one microprocessor-based subsystem (i) including at least one microprocessor, a display and a memory, (ii) configured to present information on the display and provide a digital signal representative of user-related data from a person; and (iii) arranged to establish a communication link to the central server, facilitate a communication of the user-related data on the communication link to the central server and disconnect the communication link after the communication of the physiological data has finished, wherein the server provides test and calibration sequences for the microprocessor-based subsystem after the communication link has been established by the microprocessor-based subsystem; and (c) at least one health care professional computer in signal communication with the central server to receive health-related information based on the user-related data received from the microprocessor-based subsystem and to supply data to the central server;

where the central server stores additional data received from the health care professional computer and provides the additional data to the microprocessor-based subsystem to run after the communication link has been established by the microprocessor-based subsystem.

26. The apparatus according to claim 25, wherein the microprocessor-based subsystem allows additional menus to be viewed allowing additional interactivity when the microprocessor-based subsystem is in the test and calibration sequence.

* * * * *

UNITED STATES PATENT AND TRADEMARK OFFICE

CERTIFICATE OF CORRECTION

PATENT NO. : 7,223,236 B2
APPLICATION NO. : 11/221873
DATED : May 29, 2007
INVENTOR(S) : Stephen J. Brown It is certified that error appears in the above-identified patent and that said Letters Patent is hereby corrected as shown below:

Column 23, Claim 22, line 56, replace “system” with --subsystem--

Column 24, Claim 22, line 2, replace “system” with --subsystem--

Column 24, Claim 22, line 11, replace “computer” with --apparatus--

Column 24, Claim 25, line 34, replace “physiological” with --user-related--.

Signed and Sealed this

Tenth Day of July, 2007

JON W. DUDAS
*Director of the United States Patent and Trademark Office*

US007223236C1

(12) INTER PARTES REEXAMINATION CERTIFICATE (553rd)

United States Patent

Brown

(10) Number: US 7,223,236 C1

(45) **Certificate Issued: *Mar. 12, 2013**

(54) SYSTEM AND METHOD FOR MONITORING USER-RELATED DATA FROM A PERSON

(75) Inventor: Stephen James Brown, Mountain View, CA (US)

(73) Assignee: Health Hero Network, Inc., Mountain View, CA (US)

Reexamination Request:
No. 95/000,386, Aug. 1, 2008

No. 90/010,053, Nov. 9, 2007

Reexamination Certificate for:
Patent No.: 7,223,236
Issued: May 29, 2007
Appl. No.: 11/221,873
Filed: Sep. 9, 2005

Certificate of Correction issued Jul. 10, 2007.

( * ) Notice: This patent is subject to a terminal disclaimer.

Related U.S. Application Data

(60) Division of application No. 10/605,547, filed on Oct. 7, 2003, now Pat. No. 7,264,591, which is a continuation of application No. 09/237,194, filed on Jan. 26, 1999, which is a continuation of application No. 08/481,925, filed on Jun. 7, 1995, now Pat. No. 5,899,855, which is a continuation of application No. 08/233,397, filed on Apr. 26, 1994, now abandoned, which is a continuation-in-part of application No. 07/977,323, filed on Nov. 17, 1992, now Pat. No. 5,307,263.

(51) Int. Cl.
*A61B 5/00* (2006.01)
*G06Q 10/00* (2006.01)
*G06Q 50/00* (2006.01)

(52) U.S. Cl. ............................ 600/300; 128/903; 705/2

(58) Field of Classification Search ........................ None
See application file for complete search history.

(56) References Cited

To view the complete listing of prior art documents cited during the proceedings for Reexamination Control Numbers 95/000,386 and 90/010,053, please refer to the USPTO's public Patent Application Information Retrieval (PAIR) system under the Display References tab.

*Primary Examiner* — Catherine S. Williams

(57) ABSTRACT

Monitoring airflow from a person is accomplished by using a central server arranged to receive and communicate data together with at least one microprocessor-based subsystem. The subsystem includes a microprocessor, a display and a memory. It presents information to the person on the display and processes a digital signal representing airflow from the person. Airflow-related data is communicated to the central server and, in turn, is communicated to at least one health care professional computer. The system can be used to realize systems for self-care monitoring and control of afflictions and physical conditions, such as chronic respiratory afflictions. The system can also be used together with other monitoring devices, such as glucose, blood pressure, pulse and temperature monitors, to monitor the person's condition and to communicate related data to the central server.

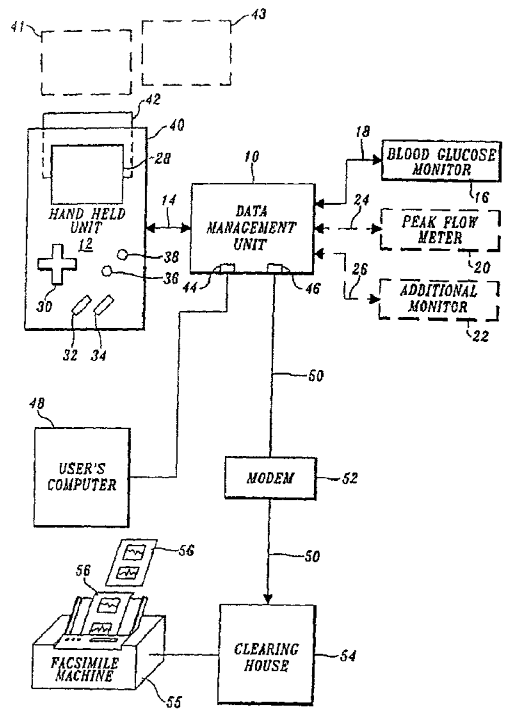

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-26 are cancelled.

* * * * *